(12) United States Patent
Toshima et al.

(10) Patent No.: US 7,267,439 B2
(45) Date of Patent: Sep. 11, 2007

(54) OPTOMETRIC APPARATUS, OPTOMETRIC METHOD, AND OPTOMETRIC SERVER

(75) Inventors: Akio Toshima, Akashi (JP); Takehiko Yoshida, Higashiosaka (JP)

(73) Assignee: Vision Optic Co., Ltd., Osaka (JP)

( * ) Notice: Subject to any disclaimer, the term of this patent is extended or adjusted under 35 U.S.C. 154(b) by 580 days.

(21) Appl. No.: 10/500,673

(22) PCT Filed: Jan. 6, 2003

(86) PCT No.: PCT/JP03/00002

§ 371 (c)(1),
(2), (4) Date: Jul. 2, 2004

(87) PCT Pub. No.: WO03/057021

PCT Pub. Date: Jul. 17, 2003

(65) Prior Publication Data

US 2005/0083485 A1  Apr. 21, 2005

(30) Foreign Application Priority Data

Jan. 4, 2002 (JP) ............................. 2002-000201
Apr. 25, 2002 (JP) ............................. 2002-125055

(51) Int. Cl.
*A61B 3/02* (2006.01)

(52) U.S. Cl. .................. 351/223; 351/239; 351/246; 600/558

(58) Field of Classification Search ........ 351/239–241, 351/246, 223, 224, 227, 237; 600/558
See application file for complete search history.

(56) References Cited

U.S. PATENT DOCUMENTS 3,574,450 A * 4/1971 White et al. ............... 351/234
RE28,921 E * 8/1976 Haines et al. .............. 351/224
4,714,330 A * 12/1987 Hennequin ................. 351/239
5,129,720 A * 7/1992 Jovicevic ................... 351/243
5,191,367 A * 3/1993 Salibello et al. ........... 351/243
5,325,136 A * 6/1994 Salibello et al. ........... 351/243
5,929,972 A * 7/1999 Hutchinson ................ 351/237
6,742,895 B2 * 6/2004 Robin ........................ 351/246

FOREIGN PATENT DOCUMENTS

| JP | 60-80431 | 5/1985 |
| JP | 62-44219 | 2/1987 |
| JP | 3-188826 | 8/1991 |
| JP | 8-66362 | 3/1996 |
| JP | 9-182722 | 7/1997 |
| JP | 2001-286442 | 10/2001 |

* cited by examiner

Primary Examiner—Evelyn A. Lester
(74) Attorney, Agent, or Firm—Keating & Bennett, LLP

(57) ABSTRACT

An optometric apparatus and an optometric method includes the steps of acquiring subject's attributes and an orientation selected by the subject on an astigmatic axis determination chart displayed on the computer screen, displaying vision measurement charts in the acquired orientation and the orientation perpendicular thereto to acquire visual recognition limits selected by the subject, calculating far point distances based on the acquired visual recognition limits and the acquired subject's attributes, and calculating a refractive power based on the acquired orientation and the calculated two far point distances. The far point distance is calculated using a neural network that has been determined by a number of subjects in advance. The astigmatic axis determination chart has four groups of a plurality of parallel lines, each group having lines arranged in their respective orientation, and the vision measurement chart has a plurality of light and dark line images of different sizes, thereby reducing the risk of presenting an erroneous refractive power.

18 Claims, 19 Drawing Sheets

Measurement of far point visual acuity

Click on the zone having three distinguishable lines. If no zones provide three distinguishable lines, click on the "No zones provide three distinguishable lines".

Measurement of near point distance

First, come as close to the screen as possible, and then go away to where you can clearly see the there lines. Measure the distance between the screen and your eyes with a scale and then input the distance in cm.

Fig. 18 (a)  Fig. 18 (b)  Fig. 18 (c)  Fig. 18 (d)  Fig. 18 (e)
 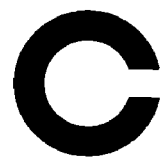 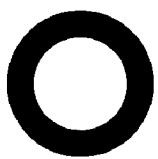 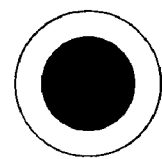 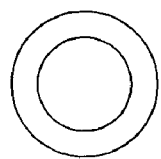
Fig. 18 (f)  Fig. 18 (g)  Fig. 18 (h)  Fig. 18 (i)
   
Fig. 18 (j)  Fig. 18 (k)  Fig. 18 (l)  Fig. 18 (m)
 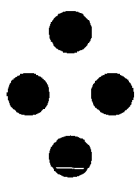  
Fig. 18 (n)  Fig. 18 (o)  Fig. 18 (p)
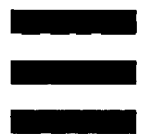 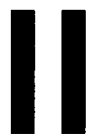 

Fig. 19
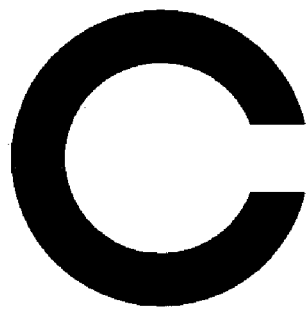
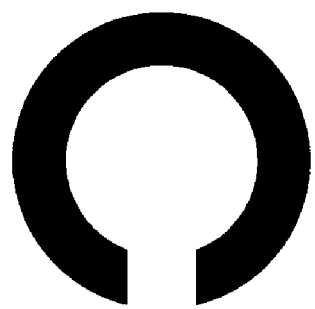
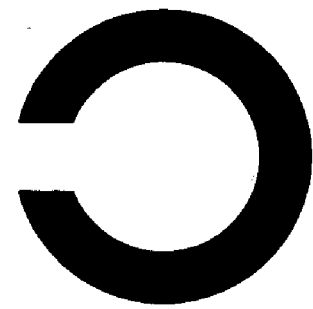
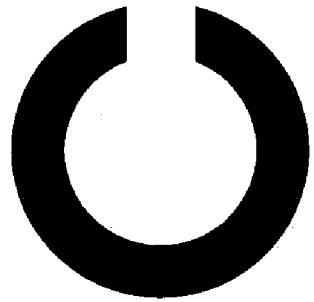

OPTOMETRIC APPARATUS, OPTOMETRIC METHOD, AND OPTOMETRIC SERVER

BACKGROUND OF THE INVENTION

1. Field of the Invention

The present invention relates to an optometric apparatus, an optometric method, and an optometric server for performing eye examinations to determine the refractive power of eyeglasses or contact lenses. More particularly, the invention relates to an optometric apparatus, an optometric method, and an optometric server for performing subjective eye examinations using a computer screen.

2. Description of the Related Art

Conventionally, a subject must go to an ophthalmologist or to an eyeglass shop to have their visual acuity examined subjectively or objectively by following examiner's instructions. Generally, to perform an objective eye examination, the examiner measures objectively the refractive coefficient of a subject's eye using an auto-refractometer and then lets the subject wear a ready-made corrective lens to check the resulting subject's visual acuity. On the other hand, to perform a subjective eye examination, using a vision test table which indicates symbols such as Landoldt rings as shown in FIG. 19, the examiner points to a symbol or character on the vision test table to determine how the symbol or the character is viewed by the subject, thereby determining the subject's visual acuity based on the subject's response.

Recently, a quantum leap has been made in ordinary household environments by the Internet. As a result, this permits consumers to check their visual acuity at home and purchase eyeglasses or contact lenses without having to go to an ophthalmologist or to an eyeglass shop.

As a matter of fact, when the consumers measure their visual acuity at home, they cannot conduct the objective eye examination because they have no test apparatus such as the auto-refractometer at home. Thus, to make measurements of visual acuity via a network such as the Internet, it is necessary to send image data to display the vision test table as shown in FIG. 19 on the screen of a subject's computer, thereby allowing the subject to determine the smallest target whose features can be visually identified by the subject.

However, generally available vision test tables are configured to display many slightly different size targets on a single screen. This configuration prevents the subject from easily making a proper determination of which target was the smallest one that could be visually clearly identified by the subject. Consequently, the subject sometimes indicated a preference for a target other than the smallest one that could be visually recognized by the subject, which results in an erroneous vision test result. Additionally, the vision test alone is not sufficient for a subject with astigmatism. Thus, an astigmatic dial as shown in FIG. 20 is conceivably presented on the computer screen to elicit from the subject a response as to the orientation in which the subject can clearly identify the dial. However, the astigmatic axis may vary depending on the distance between the subject and the computer screen, causing a simple determination of whether the orientation can be clearly identified to possibly lead to an improper determination of the astigmatic axis.

During a visual acuity measurement performed in the presence of an examiner, even a wrong response made by the subject as to his preference of targets could be checked by knowing the course of the response. However, in the absence of the examiner, it is impossible for a third party to determine whether the preference indicated by the subject is a proper or improper one.

SUMMARY OF THE INVENTION

To overcome the problems described above, preferred embodiments of the present invention provide an optometric apparatus and an optometric method for performing eye examinations, in which subjects, including those with astigmatism, are able to have an eye examination using a computer screen without requiring a special piece of equipment.

A preferred embodiment of the present invention provides an optometric apparatus for performing an eye examination using a computer screen. The apparatus includes a subject attribute acquisition unit for acquiring an attribute of a subject, an astigmatic axis determination chart display unit for displaying an astigmatic axis determination chart on the screen, an orientation acquisition unit for acquiring an orientation selected by the subject on the astigmatic axis determination chart displayed, a first vision measurement chart display unit for displaying on the screen a vision measurement chart having the acquired orientation, a first visual recognition limit acquisition unit for acquiring a visual recognition limit selected by the subject on the first vision measurement chart displayed, a second vision measurement chart display unit for displaying on the screen a vision measurement chart having an orientation perpendicular to the acquired orientation, a second visual recognition limit acquisition unit for acquiring a visual recognition limit selected by the subject on the second vision measurement chart displayed, a far point distance calculation unit for employing the acquired first visual recognition limit, the acquired second visual recognition limit, and the acquired subject attribute as entry parameters to calculate a first far point distance and a second far point distance, and a power calculation unit for calculating a refractive power based on the acquired orientation and the calculated first and second far point distances.

This configuration allows the subject attribute acquisition unit to acquire the attribute of the subject, the astigmatic axis determination chart display unit to display the astigmatic axis determination chart on the computer screen, the orientation acquisition unit to acquire an orientation selected by the subject, the first vision measurement chart display unit to display a vision measurement chart having the acquired orientation, the first visual recognition limit acquisition unit to acquire a first visual recognition limit selected by the subject, the second vision measurement chart display unit to display a vision measurement chart having an orientation perpendicular to the acquired orientation, the second visual recognition limit acquisition unit to acquire a second visual recognition limit selected by the subject, the far point distance calculation unit to employ the acquired first visual recognition limit, the acquired second visual recognition limit, and the acquired subject attribute as entry parameters to calculate a first and a second far point distance, and the power calculation unit to calculate a refractive power based on the acquired orientation and the calculated first and second far point distances. This allows subjects, including those with astigmatism, to readily have eye examinations performed via the computer screen without requiring a special piece of equipment.

Furthermore, the subject is not required to directly measure the far point distance. This provides improved operability because the subject can determine a refractive power without leaving the computer screen.

In an alternative preferred embodiment, the subject attribute acquisition unit may acquire a wearing condition desired by the subject in order to calculate a lens power that satisfies the acquired wearing condition by the power calculation unit. This allows the subject to directly place an order for eyeglasses or contact lenses based on the eye examination result.

Preferably, the first vision measurement chart display unit and the second vision measurement chart display unit include a display unit for sequentially displaying on the screen display unit a plurality of vision test charts of a combination of targets having a size level difference of two or more. Additionally, the first visual recognition limit acquisition unit and the second visual recognition limit acquisition unit include a selection unit for allowing the subject to select the smallest recognizable target on each vision test chart displayed on the screen display unit, and a determination unit for determining the subject's smallest recognizable target from the smallest recognizable targets selected on each vision test chart.

This configuration allows for sequentially displaying on the screen display unit a plurality of vision test charts of a combination of targets having a size level difference of two or more. Thus, the subject is able to select the smallest recognizable target on each vision measurement table of the combination of targets having a size level difference of two or more. It is thus possible for the subject to easily select targets. Furthermore, the subject's smallest recognizable target is determined from the smallest recognizable targets selected on each vision test chart, thereby making it possible to measure the subject's visual acuity with accuracy.

The display unit for sequentially displaying on the screen display unit a plurality of vision test charts preferably displays three vision test charts, each vision test chart including targets having a level difference of three.

Each vision test chart is made up of targets having a level difference of three, thereby further facilitating the selection of the smallest recognizable target. Furthermore, since the eye examination is made using the three vision test charts, the subject is required to select the smallest recognizable targets only three times, thereby determining the subject's smallest recognizable target. In addition, since the eye examination is made using the three vision test charts, the subject's smallest recognizable target is determined with accuracy using majority logic even when the preferences indicated by the subject are contradictory to each other. This enables accurate measurement of the subject's visual acuity.

The determination unit for determining the subject's smallest recognizable target from the smallest recognizable targets selected on each vision test chart preferably includes a determination unit for determining the smallest target in a combination of targets having a size level difference of one as the subject's smallest recognizable target when the selection unit for selecting the smallest recognizable target on each vision test chart displayed on the screen display unit has selected targets having a minimum level difference of one.

When the selection unit for selecting the smallest recognizable target on each vision test chart displayed on the screen display unit has selected targets having a minimum level difference of one, the smallest recognizable target selected by the subject is highly reliable. Thus, the smallest of the targets is determined to be the subject's smallest recognizable target, thereby permitting the subject's visual acuity to be accurately measured.

According to another preferred embodiment, the determination unit for determining the subject's smallest recognizable target from the smallest recognizable targets selected on each vision test chart includes a determination unit for determining a target between the smallest targets in combination among combinations of targets having a minimum level difference of two as the subject's smallest recognizable target when the selection unit for selecting the smallest recognizable target on each vision test chart displayed on the screen display unit has selected targets having a minimum level difference of two.

When the selection unit for selecting the smallest recognizable target on each vision test chart displayed on the screen display unit has selected targets having a minimum level difference of two, the targets having a level difference of two selected by the subject are considered to be somewhat reliable. Thus, since the smallest recognizable one of all the targets likely lies between the targets, the target between the selected targets having a level difference of two can be determined to be the subject's smallest recognizable target, thereby allowing the subject's visual acuity to be measured with sufficient accuracy.

According to still another preferred embodiment, the determination unit for determining the subject's smallest recognizable target from the smallest recognizable targets selected on each vision test chart includes a selection unit for displaying a plurality of vision test charts again on the screen display unit to allow the subject to select the smallest recognizable target on each of the plurality of vision test charts when the selection unit for selecting the smallest recognizable target on each vision test chart displayed on the screen display unit has selected targets having a minimum level difference of three or more.

When the selection unit for selecting the smallest recognizable target on each vision test chart displayed on the screen display unit has selected targets having a minimum level difference of three or more, the targets selected by the subject on each separate screen are considered to be unreliable. Thus, the system can display a plurality of vision test charts on the screen display unit again to allow the subject to select the smallest recognizable target on each of the plurality of vision test charts, thereby preventing an erroneous entry by the subject and ensuring highly accurate visual acuity measurements.

The far point distance calculation unit preferably includes a function for calculating a far point distance using a learn model which has been obtained by measurements of a number of subjects about the relationship between the subject's attribute and the visual recognition limit, and the far point distance.

As described above, this allows for calculating the far point distance using the learn model which has been obtained by measurements of a number of subjects about the relationship between the visual recognition limit and the far point distance in terms of the parameters of subjects, such as their age, sex, and height, thereby allowing the far point distance to be determined with accuracy for various subjects.

Alternatively, it is also acceptable to employ as the learn model a neural network or other artificial intelligence approaches such as the fuzzy-logical inference.

The optometric apparatus according to preferred embodiments of the present invention preferably includes a near point distance measurement chart display unit for displaying a near point distance measurement chart on the screen, and a near point distance acquisition unit for acquiring a near point distance entered by the subject on the near point distance measurement chart displayed.

As described above, the apparatus displays the near point distance measurement chart on the computer screen to acquire the near point distance measured by the subject, thereby also serving a subject even with hyperopia or presbyopia.

The acquired near point distance may also be used as an entry parameter for the far point distance calculation unit. This enables determination of the far point distance in consideration of the eyeball accommodation power of the subject, thereby determining refractive powers with increased accuracy.

The astigmatic axis determination chart display unit preferably includes a function of displaying four groups of a plurality of parallel lines, groups having lines arranged in their respective orientations.

The apparatus displays the plurality of parallel lines on a computer screen, allowing the subject with astigmatism to recognize the lines as a difference in light and dark pattern. Additionally, the limited use of the four orientations will not require the subject to make a subtle decision. This makes it possible to avoid presenting an erroneous eye examination result which would otherwise be caused by a mistaken decision by the subject.

At least one of the first vision measurement chart display unit and the second vision measurement chart display unit preferably has a function of displaying a plurality of light and dark line images having different line widths.

As described above, the apparatus displays a plurality of light and dark line images having different line widths on the computer screen, allowing the subject to enter the minimum spacing at which the light and dark line images can be recognized as a predetermined number of lines. This enables the subject to readily determine his/her visual recognition limit as compared with measuring visual acuity using Landoldt rings. In particular, a subject with good eyesight would have to view very small images on the screen, and thus can determine his/her visual recognition limit with greater accuracy by using such light and dark line images.

At least any of the astigmatic axis determination chart display unit, the first vision measurement chart display unit, and the second vision determination chart display unit preferably includes a screen display information acquisition unit for acquiring screen display information on the computer screen, and a display size rescale unit for rescaling the display size of the computer screen depending on the acquired screen display information.

This allows for acquiring screen display information such as the screen size or the resolution setting of the computer screen, and based on this information, adjusting the display sizes of the astigmatic axis determination chart or the vision measurement chart to be displayed on the computer screen. Thus, the charts to be displayed on the computer screen are automatically set to a predetermined size, thereby increasing the accuracy of the eye examinations.

Alternatively, depending on the screen display setting for the computer screen, the system may also instruct the subject to change the setting to an appropriate one or to change the distance between the subject and the computer screen. This provides appropriate instructions in accordance with the specifications of the computer used by the subject.

Alternatively, the computer screen is viewed differently depending on its type, i.e., a CRT or liquid crystal display. Thus, if any information regarding the type of computer screen is available, the system may use the information to instruct the subject to change the screen display setting or the distance between the subject and the computer screen.

As the computer screen display information, the system may acquire the entered subject attribute information or may automatically acquire the computer setting information.

At least any of the astigmatic axis determination chart display unit, the first vision measurement chart display unit, and the second vision determination chart display unit preferably includes a display color selection unit for selecting a color to be displayed on the computer screen.

This allows the subject to freely select the color of a chart to be displayed on the computer screen. Thus, for example, the system may first display a plurality of recommended sample colors, and allow the subject to select his/her preference among the sample colors to conduct an eye examination using his/her color preference.

Alternatively, since the computer screen is viewed differently depending on its type, i.e., a CRT or liquid crystal display, the system may also change the recommended color to another color for display.

At least any of the astigmatic axis determination chart display unit, the first vision measurement chart display unit, and the second vision determination chart display unit preferably includes a display brightness selection unit for selecting a brightness used for display on the computer screen.

This allows the subject to freely select the brightness of a chart to be displayed on the computer screen. Thus, for example, the system may first display a plurality of recommended brightness samples, and allow the subject to select his/her preference among the brightness samples to conduct an eye examination using his/her brightness preference.

Alternatively, since the computer screen is viewed differently depending on its type, i.e., a CRT or liquid crystal display, the system may also change the recommended brightness to another brightness for display.

According to another preferred embodiment of the present invention, an optometric method for performing an eye examination using a computer screen includes a subject attribute acquisition step for acquiring an attribute of a subject, an astigmatic axis determination chart display step for displaying an astigmatic axis determination chart on the screen, an orientation acquisition step for acquiring an orientation selected by the subject on the astigmatic axis determination chart displayed, a first vision measurement chart display step for displaying on the screen a vision measurement chart having the acquired orientation, a first visual recognition limit acquisition step for acquiring a visual recognition limit selected by the subject on the first vision measurement chart displayed, a second vision measurement chart display step for displaying on the screen a vision measurement chart having an orientation perpendicular to the acquired orientation, a second visual recognition limit acquisition step for acquiring a visual recognition limit selected by the subject on the second vision measurement chart displayed, a far point distance calculation step for employing the acquired first visual recognition limit, the acquired second visual recognition limit, and the acquired subject attribute as entry parameters to calculate a first far point distance and a second far point distance, and a power calculation step for calculating a refractive power based on the acquired orientation and the calculated first and second far point distances.

According to this configuration, the method provides the steps of acquiring an attribute of the subject as well as an orientation selected by the subject on an astigmatic axis determination chart displayed on the computer screen, displaying a vision measurement chart having the acquired orientation to acquire a first visual recognition limit selected by the subject, displaying a vision measurement chart having an orientation perpendicular to the acquired orientation to acquire a second visual recognition limit selected by the subject, calculating a first far point distance and a second far point distance with the acquired first and second visual recognition limits and the acquired subject attributes being employed as entry parameters, and calculating a refractive power based on the acquired orientation and the calculated first and second far point distances. Thus, subjects, including those with astigmatism, can readily make eye examinations using the computer screen without requiring a special piece of equipment.

Furthermore, the subject is not required to directly measure the far point distance. This allows for providing improved operability because the subject can determine a refractive power without leaving the computer screen.

In the optometric method according to this preferred embodiment of the present invention, the first and the second vision measurement chart display steps preferably include a display step for sequentially displaying on screen display unit a plurality of vision test charts of a combination of targets having a size level difference of two or more. Additionally, the first visual recognition limit acquisition step and the second visual recognition limit acquisition step preferably include a selection step for allowing the subject to select the smallest recognizable target on each vision test chart displayed on the screen display unit, and a determination step for determining the subject's smallest recognizable target from the smallest recognizable targets selected on each vision test chart.

The method allows for sequentially displaying on the screen display unit a plurality of vision test charts of a combination of targets having a size level difference of two or more. Thus, the subject is allowed only to select the smallest recognizable target on each vision measurement table of a combination of targets having a size level difference of two or more, thereby making it possible for the subject to easily select targets. Furthermore, the subject's smallest recognizable target is determined from the smallest recognizable targets selected on each vision test chart, thereby making it possible to measure the subject's visual acuity with accuracy.

A preferred embodiment of the present invention provides an optometric apparatus for performing an eye examination, which displays on a screen display unit a vision test chart including a plurality of targets having sizes varied in a stepwise manner corresponding to visual acuity and allows a subject to select the smallest recognizable target on the vision test chart displayed on the screen display unit, thereby allowing the subject to subjectively measure subject's visual acuity. The apparatus includes a vision test chart display unit for sequentially displaying on the screen display unit a plurality of vision test charts of a combination of targets having a size level difference of two or more, a distinctive recognizable target acquisition unit for acquiring the smallest recognizable target selected by the subject on each vision test chart displayed by the vision test chart display unit, and a recognizable target determination unit for determining the subject's smallest recognizable target from each distinctive recognizable target acquired by the distinctive recognizable target selection unit.

An apparatus according to a preferred embodiment preferably provides an optometric server for performing an eye examination, which provides a vision test chart to a client terminal connected to a network, the chart including a plurality of targets having sizes varied in a stepwise manner corresponding to visual acuity, and allows a subject to select the smallest recognizable target on the vision test chart displayed on screen display unit of the client terminal, thereby allowing the subject to subjectively measure his visual acuity. The server includes a vision test chart image data provision unit for providing vision test chart image data such that a plurality of vision test charts of a combination of targets having a size level difference of two or more are displayed sequentially on the screen display unit of the client terminal, a distinctive recognizable target acquisition unit for acquiring the smallest recognizable target selected by the subject on each vision test chart displayed on the screen display unit of the client terminal, and a recognizable target determination unit for determining the subject's smallest recognizable target from each distinctive recognizable target acquired by the distinctive recognizable acquisition unit.

This configuration enables sequential displaying on the screen display unit of a plurality of vision test charts of a combination of targets having a size level difference of two or more. Thus, the subject is allowed only to select the smallest recognizable target on each vision measurement table of the combination of targets having a size level difference of two or more. It is thus possible for the subject to easily select targets. Furthermore, the subject's smallest recognizable target is determined from the smallest recognizable targets selected on each vision test chart, thereby making it possible to accurately measure the subject's visual acuity.

Another preferred embodiment of the present invention provides an optometric server for performing an eye examination using a computer screen to a client computer connected to a network. The server includes a subject attribute acquisition unit for acquiring an attribute of a subject, an astigmatic axis determination chart display unit for displaying an astigmatic axis determination chart on the screen, an orientation acquisition unit for acquiring an orientation selected by the subject on the astigmatic axis determination chart displayed, a first vision measurement chart display unit for displaying on the screen a vision measurement chart having the acquired orientation, a first visual recognition limit acquisition unit for acquiring a visual recognition limit selected by the subject on the first vision measurement chart displayed, a second vision measurement chart display unit for displaying on the screen a vision measurement chart having an orientation perpendicular to the acquired orientation, a second visual recognition limit acquisition unit for acquiring a visual recognition limit selected by the subject on the second vision measurement chart displayed, a far point distance calculation unit for employing the acquired first visual recognition limit, the acquired second visual recognition limit, and the acquired subject attribute as entry parameters to calculate a first far point distance and a second far point distance, and a power calculation unit for calculating a refractive power based on the acquired orientation and the calculated first and second far point distances.

This permits sequential displaying on the screen display unit of a plurality of vision test charts of a combination of targets having a size level difference of two or more. Thus, the subject is allowed only to select the smallest recognizable target on each vision measurement table of a combination of targets having a size level difference of two or more. It is thus possible for the subject to easily select targets. Furthermore, the subject's smallest recognizable target is determined from the smallest recognizable targets selected on each vision test chart, thereby making it possible to accurately measure the subject's visual acuity.

These and other elements, steps, characteristics, features and advantages of the invention will be more readily apparent from the following detailed description of the invention taken in conjunction with the accompanying drawings.

BRIEF DESCRIPTION OF THE DRAWINGS

FIG. 18 is a view showing exemplary targets applicable to preferred embodiments of the present invention;

FIG. 19 is a view showing an example of Landoldt rings; and

DETAILED DESCRIPTION OF PREFERRED EMBODIMENTS

Figure 1:
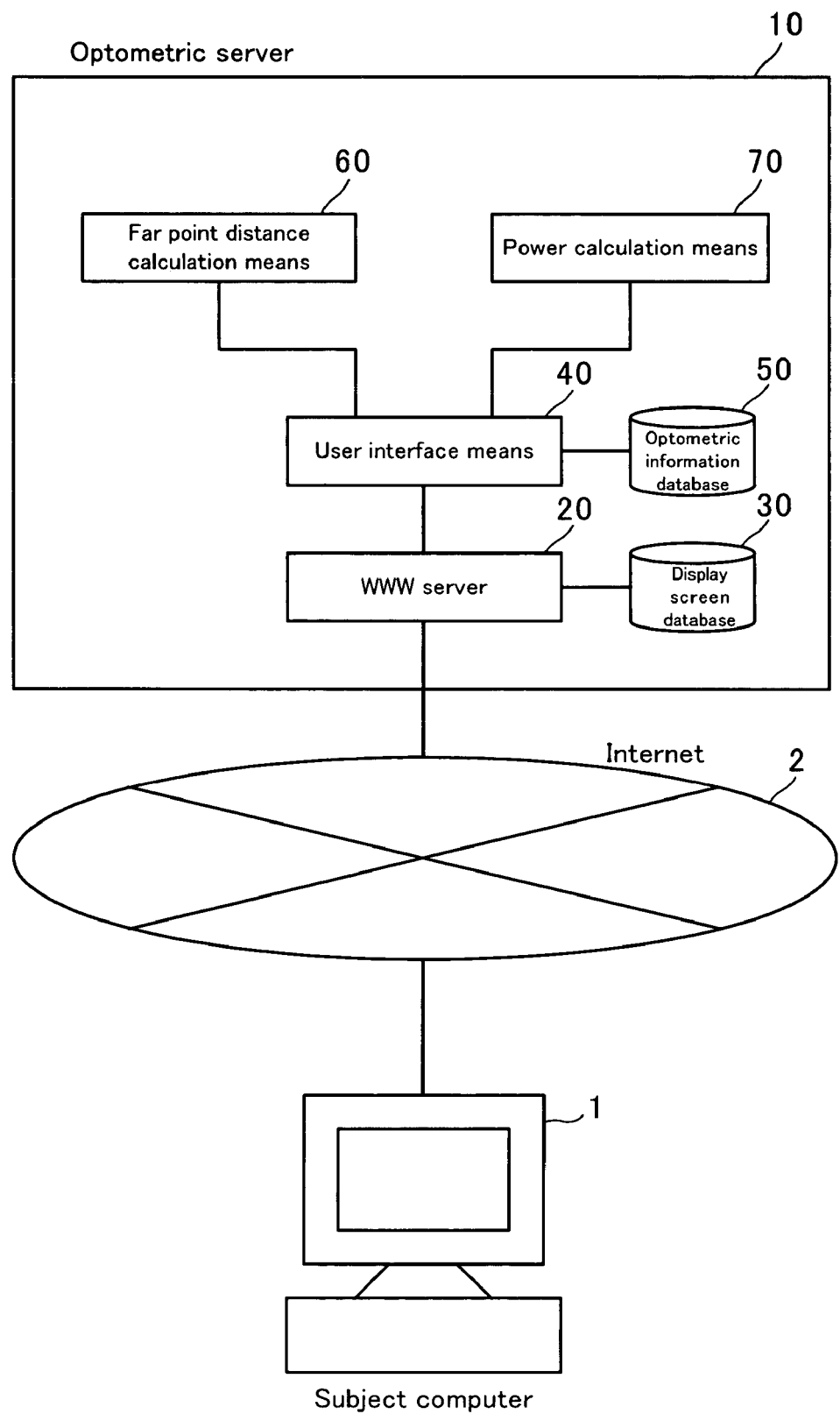
FIG. 1 is a view showing the system configuration of an optometric apparatus according to a preferred embodiment of the present invention.

FIG. 1 shows the system configuration of an optometric apparatus according to a preferred embodiment of the present invention.

As illustrated, in this system, a computer 1 used by a subject is connected via the Internet 2 to an optometric server 10 for providing an optometric method according to preferred embodiments of the present invention.

The optometric server 10, which provides an optometric service to the subject computer 1 via the Internet 2, includes a WWW server 20, a display screen database 30, a user interface unit 40, an optometric information database 50, a far point distance calculation unit 60, and a power calculation unit 70.

When accessed by the subject computer 1, the WWW server 20 provides an optometric function according to an optometric procedure of the present invention. In this preferred embodiment, an HTTP server is used such that the subject computer 1 is served using a general Web browser.

In accordance with the optometric procedure of preferred embodiments of the present invention, the display screen database 30 stores screen data that is presented by the WWW server 20 to the subject computer having access thereto. In this preferred embodiment, a start-up guidance screen, a subject's attribute entry screen, an astigmatic axis determination screen, a far point vision measurement screen, and a near point vision measurement screen are stored in the HTML format.

Based on the information entered by the subject on a screen displayed by the WWW server 20 on the subject computer 1, the user interface unit 40 stores a subject's attributes in the optometric information database 50, starts the far point distance calculation unit 60 to calculate far point distances, and starts the power calculation unit 70 to calculate refractive powers.

The user interface unit 40 is a process activated by the WWW server 20 via a CGI (Common Gateway Interface), while the far point distance calculation unit 60 and the power calculation unit 70 are processes activated by the user interface unit 40. The optometric information database 50 also stores a subject's attribute data entered by the subject, data indicative of a preference for an orientation on an astigmatic axis determination chart (the right and left eyes), data indicative of a visual recognition limit on a vision measurement chart (the right and left eyes times two orientations), data indicative of a near point distance on a near point distance measurement chart (the right and left eyes times two orientations), calculated far point distances (the right and left eyes times two orientations), and calculated refractive powers (the right and left eyes).

Figure 2:
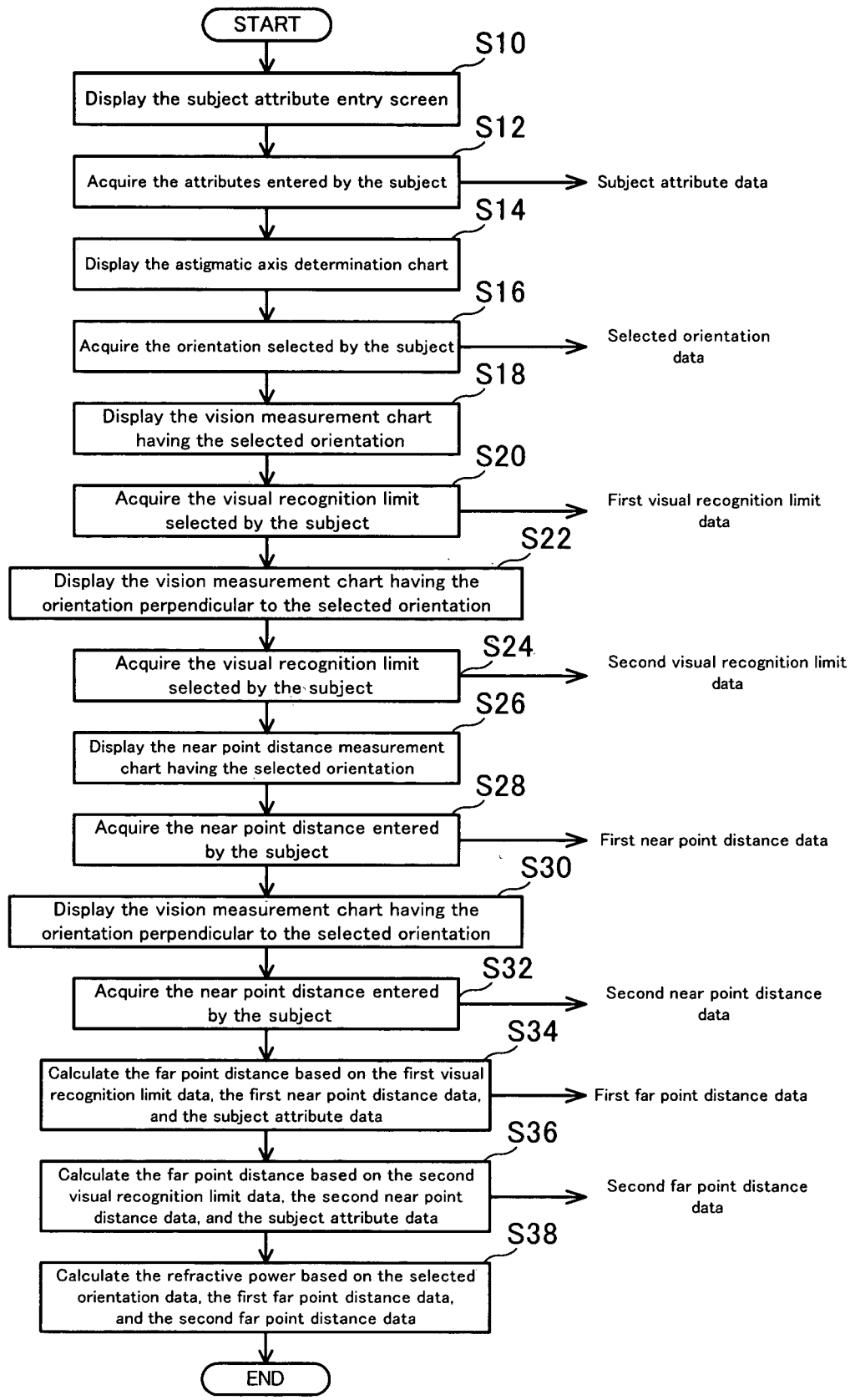
FIG. 2 is a process flowchart followed by an optometric apparatus according to a preferred embodiment of the present invention.

Now, by way of example, an optometric procedure followed by such an optometric system will be described below with reference to FIG. 2.

Figure 3:
FIG. 3 is a view showing a display example of a personal information entry screen.
Figure 4:
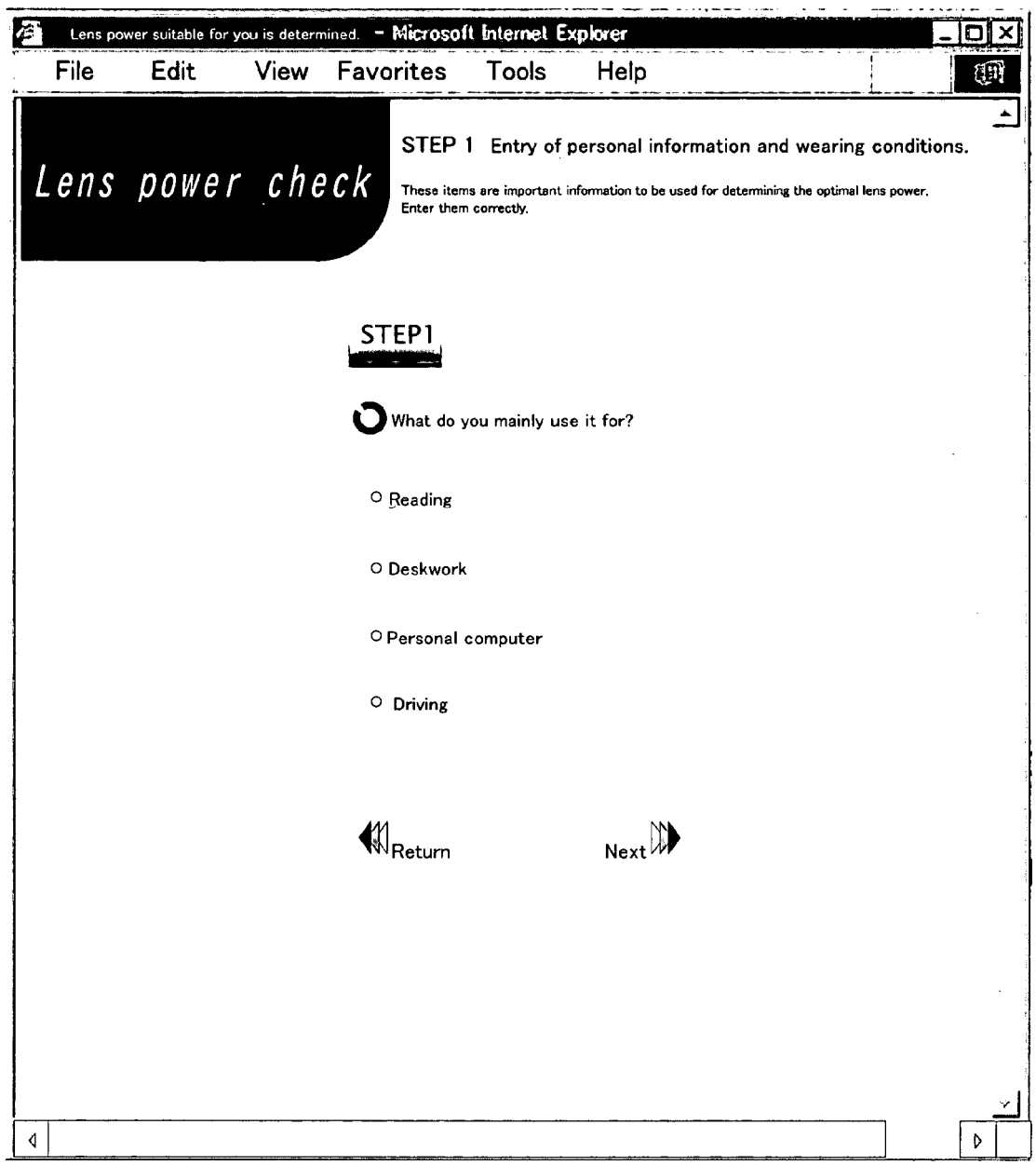
FIG. 4 is a view showing a display example of a wearing condition entry screen.

First, the system displays a subject attribute entry screen (S10) to acquire attributes entered by a subject and then stores the acquired attributes as subject data (S12). The attributes of the subject include personal information such as their age, sex, and height, and wearing condition information regarding the situations in which the eyeglasses or the contact lenses are mainly used. FIG. 3 shows an exemplary display screen employed upon acquiring the personal information, FIG. 4 shows an exemplary display screen used upon acquiring wearing conditions. In this preferred embodiment, the wearing conditions "reading" and "deskwork" are assumed for near distances, while "personal computer" is assumed for intermediate distances and "driving" for far distances.

Figure 5:
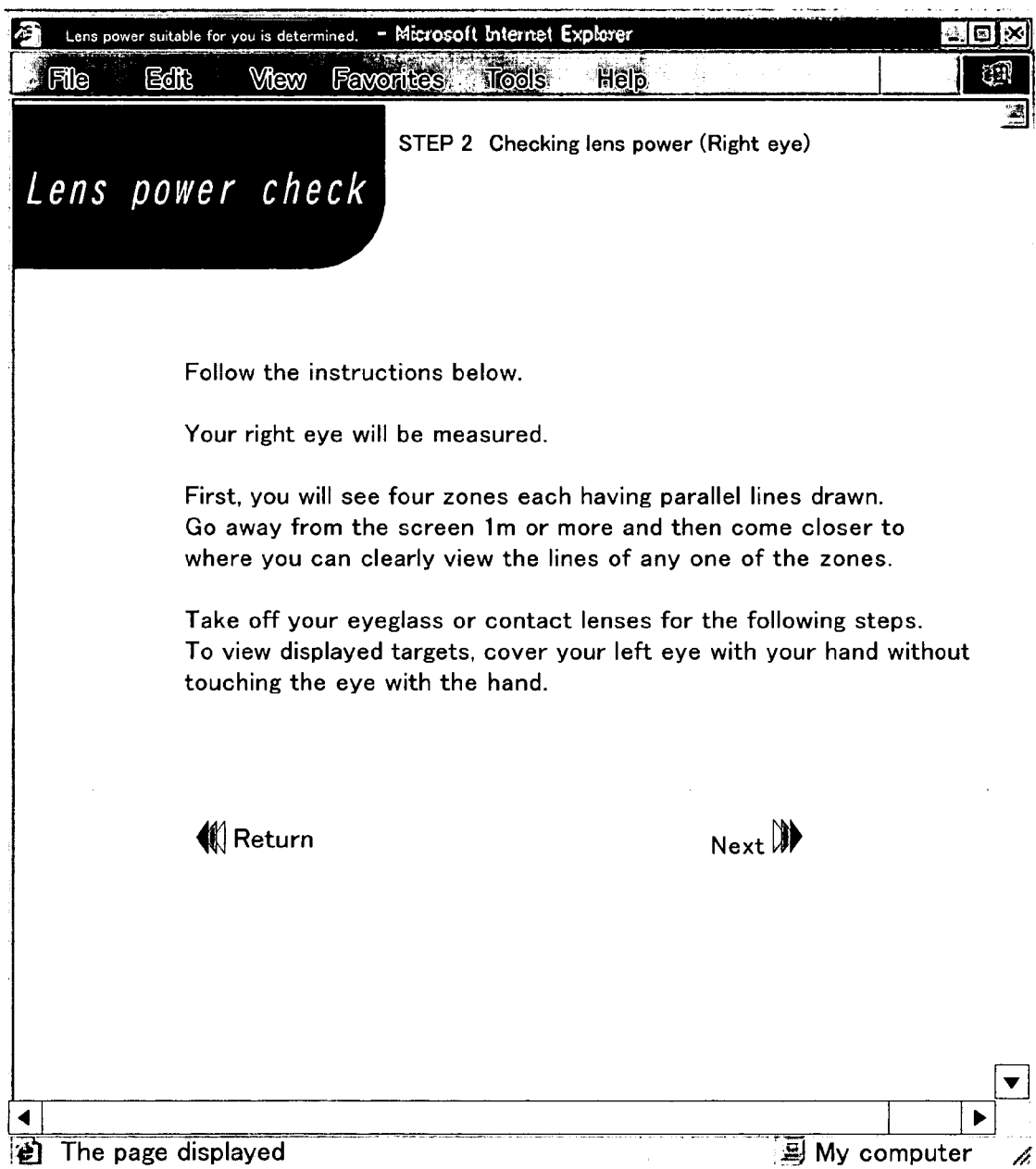
FIG. 5 is a view showing a display example of a screen for explaining how to determine an astigmatic axis.
Figure 6:
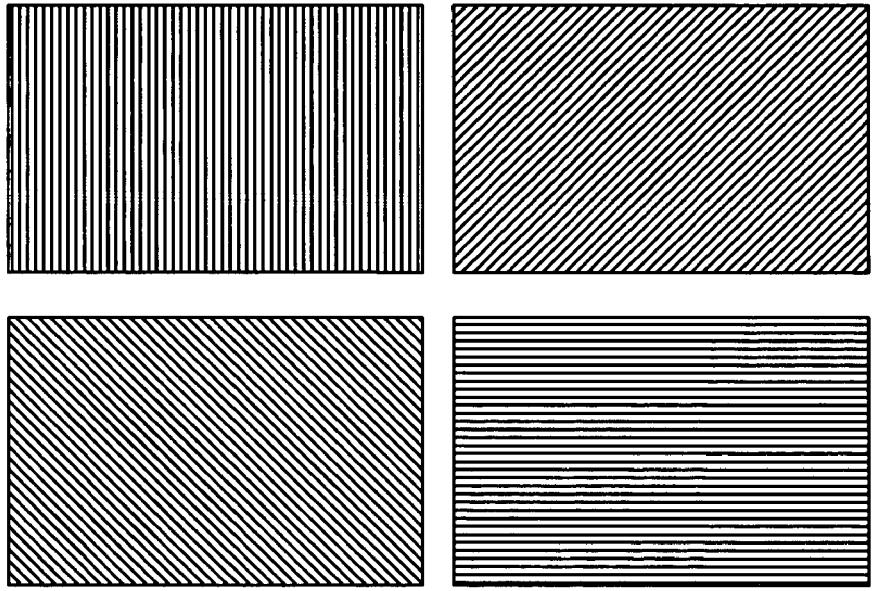
FIG. 6 is a view showing a display example of an astigmatic axis determination screen.

Then, the system displays an astigmatic axis determination chart for determining an astigmatic axis (S14) and acquires the orientation selected by the subject, which is then stored as the selected orientation data (S16). FIG. 5 shows an exemplary screen for explaining how to determine an astigmatic axis, FIG. 6 showing an exemplary astigmatic axis determination screen.

As illustrated, the astigmatic axis determination chart is made up of four groups of a plurality of parallel lines, each group having lines arranged in one orientation at an angle of 45 degrees, 90 degrees, 135 degrees, and 180 degrees, respectively. A subject with astigmatism may view the charts clearly in one orientation while viewing other charts vaguely in another orientation. Thus, the system prompts the subject to click on the zone in the orientation which the subject views differently. As described above, the system allows the subject to select differently viewed orientations. This is because the clearly viewed orientation may vary depending on the distance between the subject and an object, thus allowing for selecting only the clearly viewed orientation may lead to an erroneous decision being made on the astigmatic axis. Accordingly, preferred embodiments of the present invention are designed to make a decision on the major astigmatic axis not at this stage but at a later time by finding a far point distance.

A subject without astigmatism may view all of the orientations clearly. Thus, the subject who has clicked on "All zones viewed equally well" or "Indistinguishable" is considered to have no astigmatism and undergoes the following measurements only in the horizontal orientation.

The astigmatic axis determination chart has a green background with black lines having a line width of two pixels and a width between the lines of three pixels. A white background may cause a miosis and a greater depth of field in the eyes due to its excessive brightness, thus reducing viewing differences in the four zones. This is why an eye-friendly green based color is used to reduce brightness. Black lines were employed because a number of subjects who have undergone an optometric experiment showed comfort in viewing black lines. The lines have a width of at least two pixels because lines of a width of one pixel may be viewed differently in the horizontal, vertical, and oblique orientations particularly in the case of a CRT display due to focus blurring caused by the electron gun. The width between the lines was set such that the spacing between the lines could be identified at a distance of 1 m because an extremely short distance to the chart in the determination of astigmatism would cause the astigmatic axis to vary, possibly resulting in an error in the determination. An eyesight of 1.0 (an angle of view of 1 minute) indicates the ability to distinguish an opening of 0.29 mm at a distance of 1 m, which generally corresponds to one pixel on a 14-inch liquid crystal display or a 17-inch CRT. Therefore, two pixels correspond to an eyesight of approximately 0.5. However, since subjects who take the eye examination need eyeglasses, the spacing was further increased to three pixels. On the other hand, the four astigmatic axis orientations were employed because the four orientations allow the subject to select sufficiently practical eyeglasses or contact lenses, and for the subject to make decisions by himself, it is necessary to do so as easily as possible without any error.

Figure 7:
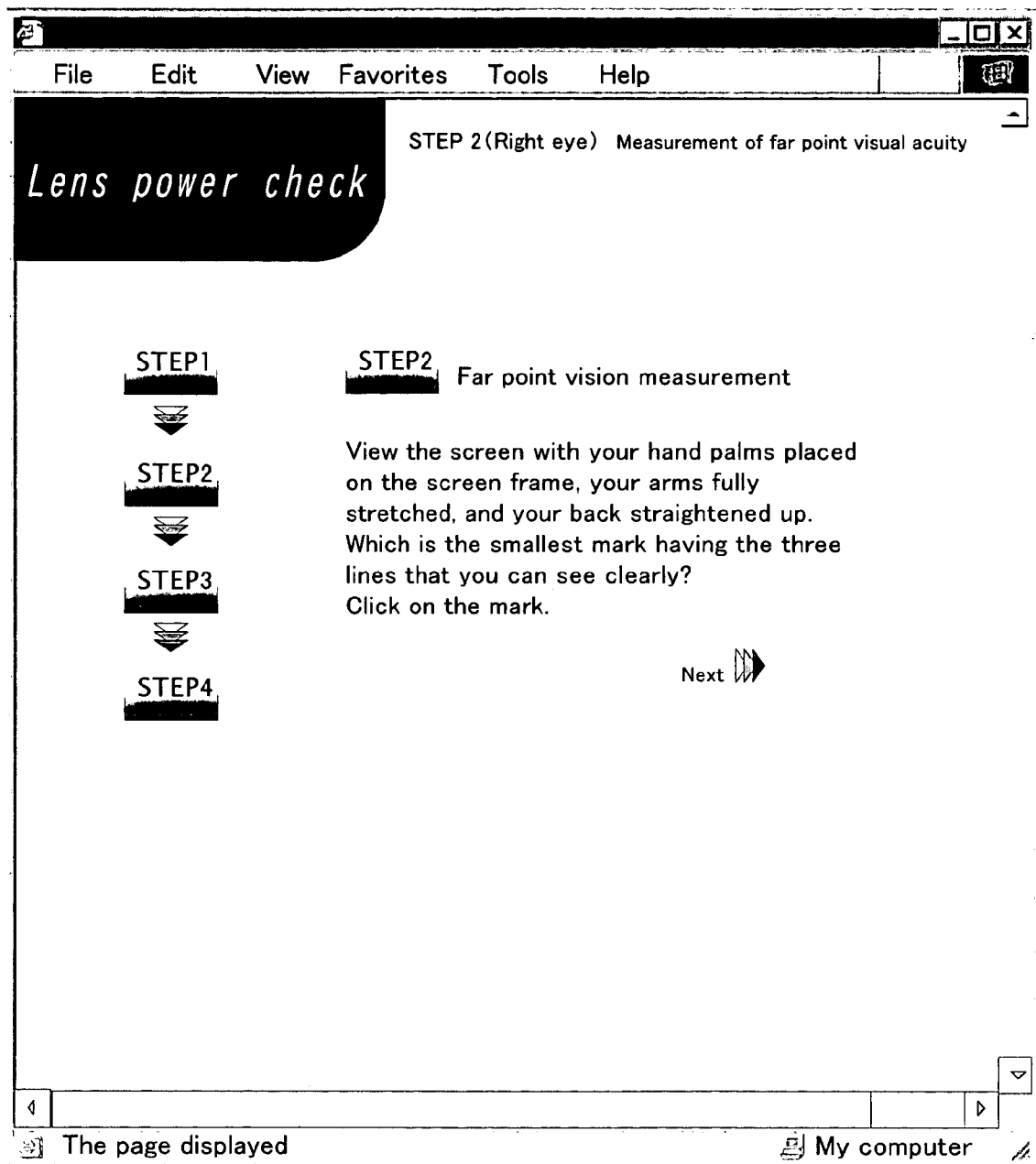
FIG. 7 is a view showing a display example of a screen for explaining how to measure a far point visual acuity.
Figure 8:
FIG. 8 is a view showing a display example of a far point vision measurement screen.

Then, to measure the far point vision in the orientation selected by the subject, the system displays the vision measurement chart having the selected orientation (S18), and acquires the visual recognition limit selected by the subject, which is then stored as first visual recognition limit data (S20). FIG. 7 shows an exemplary screen for explaining how to measure a far point visual acuity, FIG. 8 showing an example of the far point vision measurement screen.

As illustrated, the vision measurement chart (target) is a light and dark line image made up of three black lines and two white lines of a certain line width. The system displays a plurality of charts (targets), in each of which the width of the lines is varied in I steps (from approximately 10 steps to 20 steps) corresponding to visual acuity. On the vision measurement charts, the system prompts the subject to click on the smallest mark in which the subject can distinguish its three lines. Since the subject is allowed to select the mark in which the subject can distinguish its three lines, the subject can make a determination more easily as compared with the case of the Landoldt ring in which the subject is required to visually identify a single gap.

Here, the system instructs the subject to measure the far point vision on the computer screen at his reach. This is because the length of the arm is approximately proportional to the height, and thus the distance between the subject and the chart can be predicted based on the data on the height entered in advance.

It can thus be seen that the measurement can be readily carried out because the subject is not required either to measure the distance to the computer screen or rescale the screen display size.

Likewise, to measure the far point visual acuity in the orientation perpendicular to the orientation selected by the subject, the system displays the vision measurement chart having the orientation perpendicular to the selected orientation (S22), and then acquires the visual recognition limit selected by the subject to be stored as second visual recognition limit data (S24).

Figure 9:
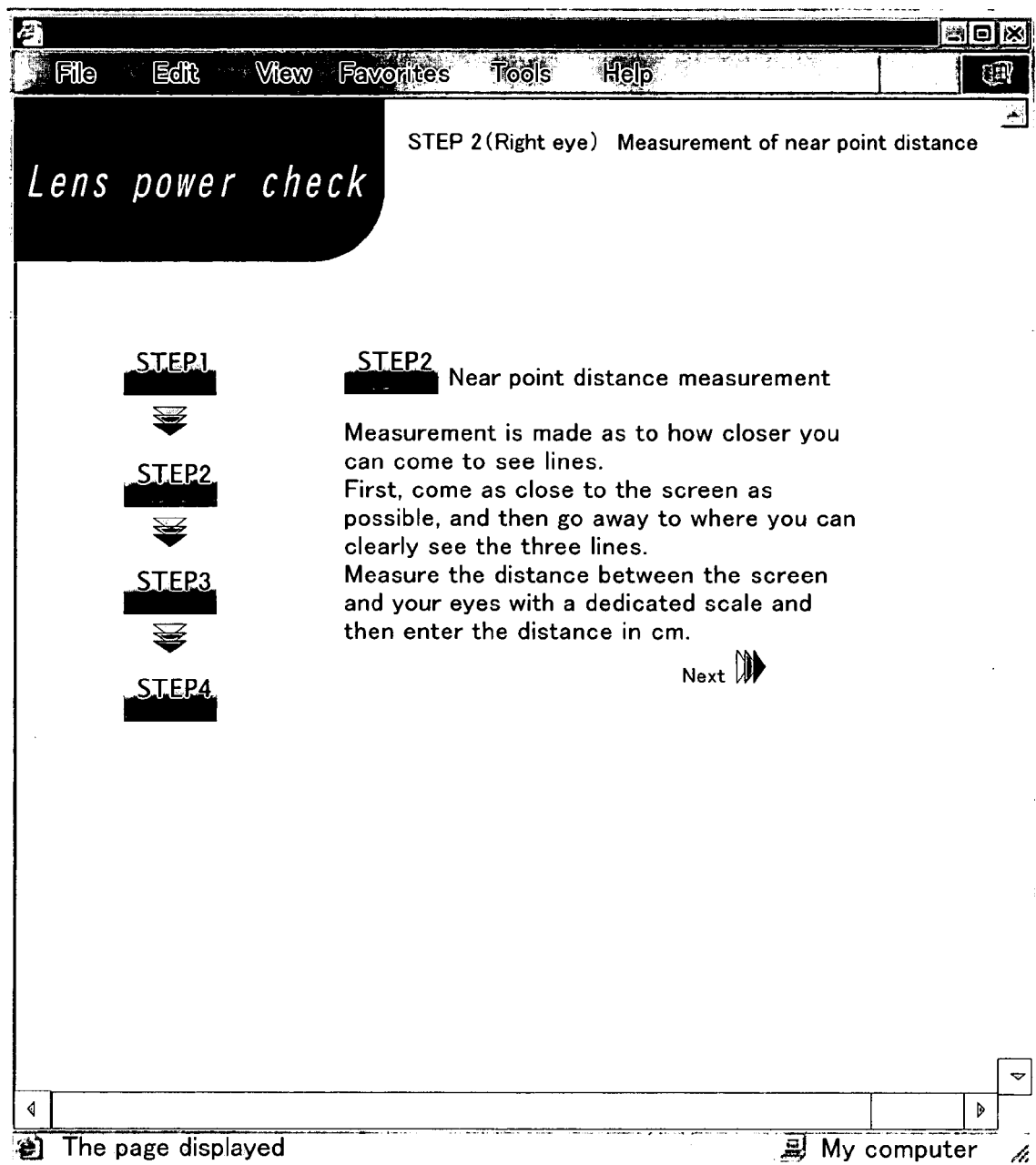
FIG. 9 is a view showing a display example of a screen for explaining how to measure a near point distance.
Figure 10:
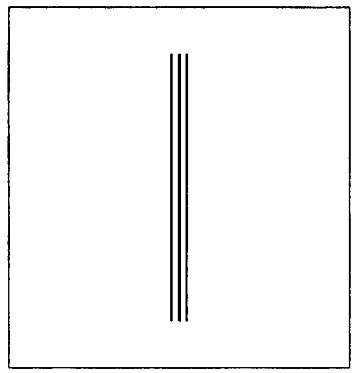
FIG. 10 is a view showing a display example of a near point distance measurement screen.

Then, to measure the near point distance in the orientation selected by the subject, the system displays a near point distance measurement chart having the selected orientation (S26) and stores the near point distance entered by the subject as first near point distance data (S28). FIG. 9 shows an exemplary screen for explaining how to measure a near point distance. FIG. 10 shows an exemplary near point measurement screen.

As illustrated, the near point distance measurement chart (target) has three black lines provided in a green background. The message on the screen instructs the subject to move as close to the screen as possible and then move away therefrom until the subject can clearly see the three lines, where the subject is prompted to measure the distance between the eye and the screen and input the resulting distance in centimeters.

The near point distance measurement chart (target) uses thinner lines as compared with the aforementioned vision measurement chart to allow the subject to visually identify the chart in close proximity to the computer screen. However, because of differences in resolution due to the age, thinner lines are used for younger subjects and slightly bolder lines are used for middle aged and elderly subjects.

Likewise, to measure the near point distance in the orientation perpendicular to the orientation selected by the subject, the system displays a near point distance measurement chart having the selected orientation (S30) and then stores the near point distance entered by the subject as second near point distance data (S32).

Then, the system determines a far point distance from the first visual recognition limit data, the first near point distance data, and the subject limit data to store the resulting far point distance as first far point distance data (S34).

Likewise, the system determines another far point distance from the second visual recognition limit data, the second near point distance data, and the subject limit data to store the resulting another far point distance as second far point distance data (S36).

Figure 11:
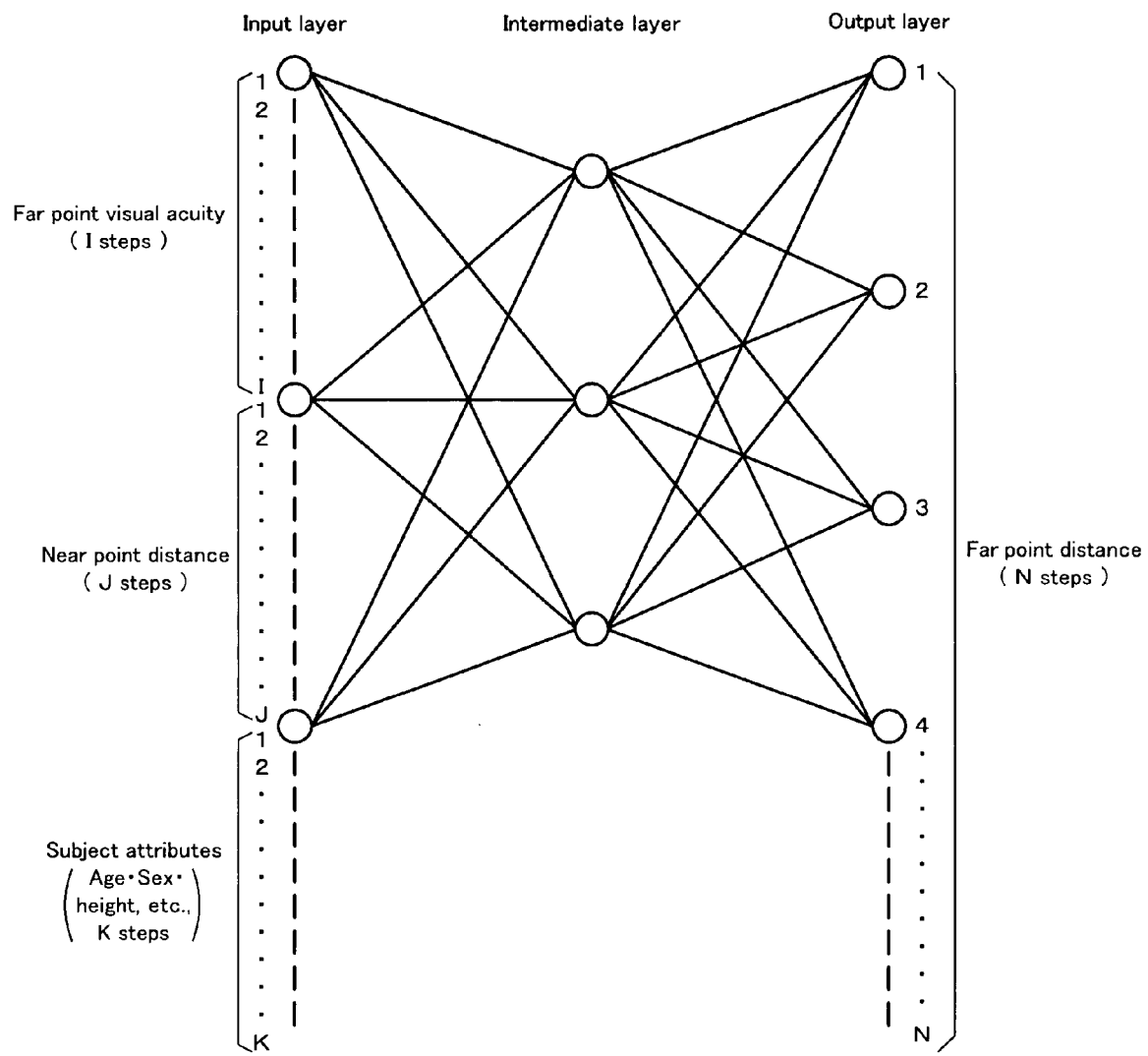
FIG. 11 is a view showing an exemplary configuration of a neural network for calculating far point distances.

The far point distance is calculated using a neural network that has been taught by a number of subjects in advance. FIG. 11 illustrates an exemplary configuration of a neural network for calculating the far point distance. As illustrated, the input layer has I steps of far point visual acuity (the visual recognition limit selected by the subject on the vision measurement chart), J steps of near point distance (the near point distance measured by the subject on the near point distance measurement chart), and K steps of subject's attributes (their age, sex, and height), while the output layer has N steps of far point distance. The age and sex are employed as parameters because the accommodation power of the subject's eyes varies due to these parameters. On the other hand, as described above, the height that is proportional to the length of the arm is used as a substitute parameter in order to adjust the distance between the subject and the screen to the length of the arm. As a learning method, the so-called back-propagation method was used.

Here, the near point distance of the entry parameters and the calculated far point distance are each converted into the value D (diopter) or the reciprocal of the distance measured in meters for ease of conversion of them into lens powers.

The neural network was designed to produce two independent learning models in the selected orientation of the astigmatic axis and the orientation perpendicular to the selected orientation and to be employed individually for calculations.

Since a screen is viewed differently depending on the type of displays, the calculations were performed using such a neural network that had been taught independently depending on the type of the display, either a CRT or liquid crystal display.

The aforementioned steps from the astigmatic axis determination (S14) to the far point distance calculation (S36) are performed for both the right and left eyes. Then, based on the resulting selected orientation data, the first far point distance data, and the second far-point distance data, the system calculates a refractive power (S=spherical refractive power, C=astigmatic refractive power, and AX=astigmatic axis) (S38).

Assuming that D1 is the first far point distance determined in S34 in the orientation of AX1, and D2 is the second far point distance determined in S36 in the orientation of AX2, the following relationships are given:

S=D1, C=D2−D1, and AX=AX1 when |D1|<|D2|, and
S=D2, C=D1−D2, and AX=AX2 when |D2|<|D1|.

As described above, in the aforementioned preferred embodiment, such a case has been described in which only the refractive power of eyes is calculated. However, the refractive power of an eye determined and the wearing condition of the subject attribute data may also be used to determine the lens power so as to place an order for an eyeglass or contact lenses.

In this case, based on the wearing condition of the subject attribute data, a normal service distance is determined from among the near distance (30 cm), the intermediate distance (50 to 60 cm), and the far distance (5 m), thereby determining the power of the recommended lens.

For example, in the case of the far distance lens, the far point distance D1 is corrected to 5 m (−0.2D), such that the power of the recommend lens is D1+0.2D.

In addition, the system may include an optical eyeball model generation unit for generating an optical eyeball model based on the refractive power calculated by the power calculation unit and subject's attributes and a naked-eye light-gathering capability check unit for checking the light-gathering capability of naked eyes using the generated optical eyeball model in order to check the validity of the calculated refractive power. This allows for determining power with greater accuracy.

Another preferred embodiment preferably includes a corrected light-gathering capability calculation unit for calculating the light-gathering capability provided by the correction made with the recommended lens using the generated eyeball model in order to determine the recommended lens. This provides a more suitable lens power for the subject.

Furthermore, the system may also include a sharpness calculation unit for calculating the sharpness at a predetermined distance based on the light-gathering condition provided when the subject wears the recommended lenses, image sample generation unit for generating an image sample at the sharpness calculated, and image sample display unit for displaying on a computer screen the image sample generated, in which the subject is allowed to check the image sample under the condition of wearing the recommended lens. The subject is thus allowed to check the viewing under the condition of wearing the recommended lenses, thereby making it possible to determine a more suitable lens power.

As described above, in the aforementioned preferred embodiment, using a neural network that has been taught by a number of subjects, the far point distance calculation unit determines the far point distance based on the far point visual acuity, the near point distance, and the subject's attributes. However, the present invention is not limited thereto. It is also acceptable to calculate the far point distance using the fuzzy inferences, allowing membership functions or inference rules to be determined based on data on a large number of subjects. Alternatively, based on data on a number of subjects, an approximate equation to express the relationship between the far point visual acuity and the far point distance may be determined using parameters such as the near point distance and subject's attributes and used to calculate the far point distance. This also achieves the advantages of preferred embodiments of the present invention.

In the aforementioned preferred embodiment, the near point distance is employed as an entry parameter in the calculation of the far point distance. However, the present invention is not limited thereto. Alternatively, the near point distance may be eliminated. Even in this case, since the near point distance has the characteristic of being proportional to the age, this also achieves the advantages of the present invention.

As described above, the aforementioned preferred embodiment provides the astigmatic axis determination chart having four groups of a plurality of parallel lines displayed on a single screen, each group having lines arranged in their respective orientations, allowing the subject to select a zone that is viewed differently from the others. However, the present invention is not limited thereto. Alternatively, the four groups of lines arranged in their respective orientations may be displayed each in sequence allowing the subject to select the orientations that are viewed differently.

The aforementioned preferred embodiment provides the vision measurement chart having a plurality of different size charts (targets) displayed in sequence on a single screen, allowing the subject to select the visual recognition limit. However, the present invention is not limited thereto. Alternatively, the charts (targets) of different sizes may be displayed in a descending order, allowing the subject to select the chart that cannot be visually identified for the first time.

In the case of the vision measurement chart having a plurality of different size charts (targets) displayed in sequence a signal screen, allowing the subject to select the visual recognition limit, the system may also be configured such that a plurality of vision test charts of a combination of charts (targets) having a size level difference of two or more may be displayed sequentially on the screen, allowing the subject to select the recognizable charts (target).

Now, the configuration of an optometric system for performing such an optometric method and its process flow will be described below.

Figure 12:
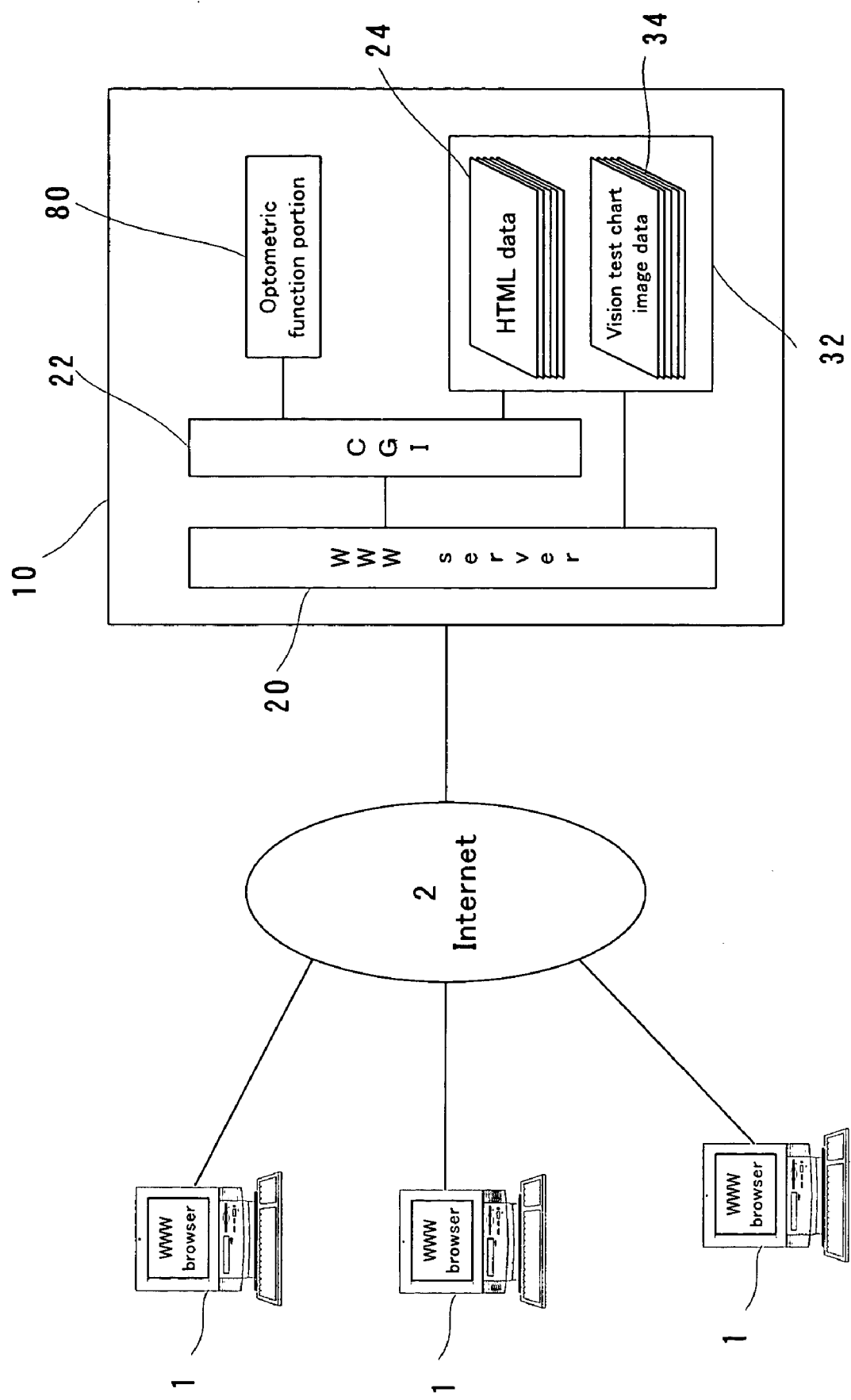
FIG. 12 is a schematic view showing part of an optometric system according to another preferred embodiment of the present invention.

FIG. 12 is a schematic view showing part of an optometric system according to another preferred embodiment of the present invention. Similar to the aforementioned preferred embodiment, as shown in FIG. 12, this optometric system includes the optometric server 10, the subject computer 1, and the Internet 2.

The optometric server 10 includes the WWW server 20 which serves as a vision test chart image data provision unit. The WWW server 20 is a server application that transmits and receives data to and from the subject computer 1 in accordance with the HTTP protocol.

The WWW server 20 is connected with a CGI 22. The CGI 22 selects HTML data, described later, corresponding to the contents of the HTML data transmitted by a subject, and changes the contents of the HTML data for dynamic transmission. Furthermore, the CGI 22 functions as a distinctive recognizable target acquisition unit for extracting a given piece of data from the HTML data which includes the data entered on the subject computer 1 to pass the data on the extracted and acquired target to an optometric function portion 80, described later.

A storage area 32 on which the WWW server 20 reads various types of data stores vision test chart image data 34. The vision test chart image data 34 includes a plurality of pieces of vision test chart image data 34. The vision test chart image data 34 or image data in HTML data 24 is transmitted as appropriate to the subject computer 1 and displayed on the display device of the subject computer 1.

Figure 13:
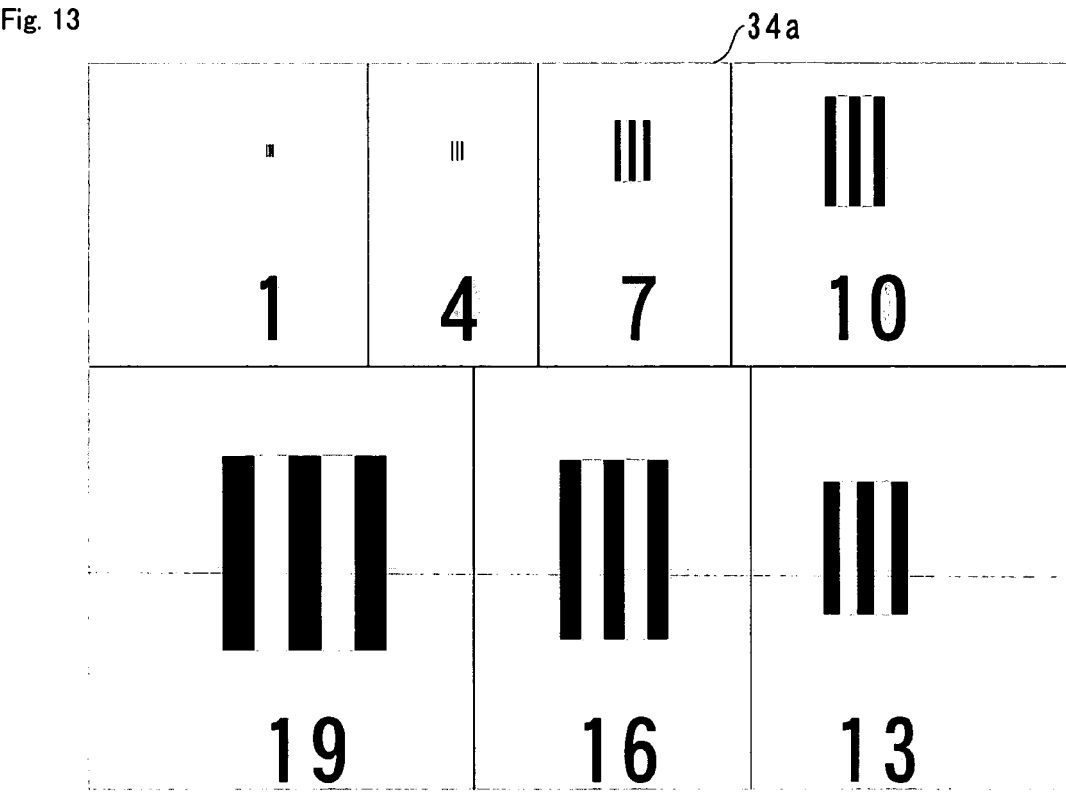
FIG. 13 is a schematic view showing vision test chart image data indicative of an arrangement of a plurality of targets.
Figure 14:
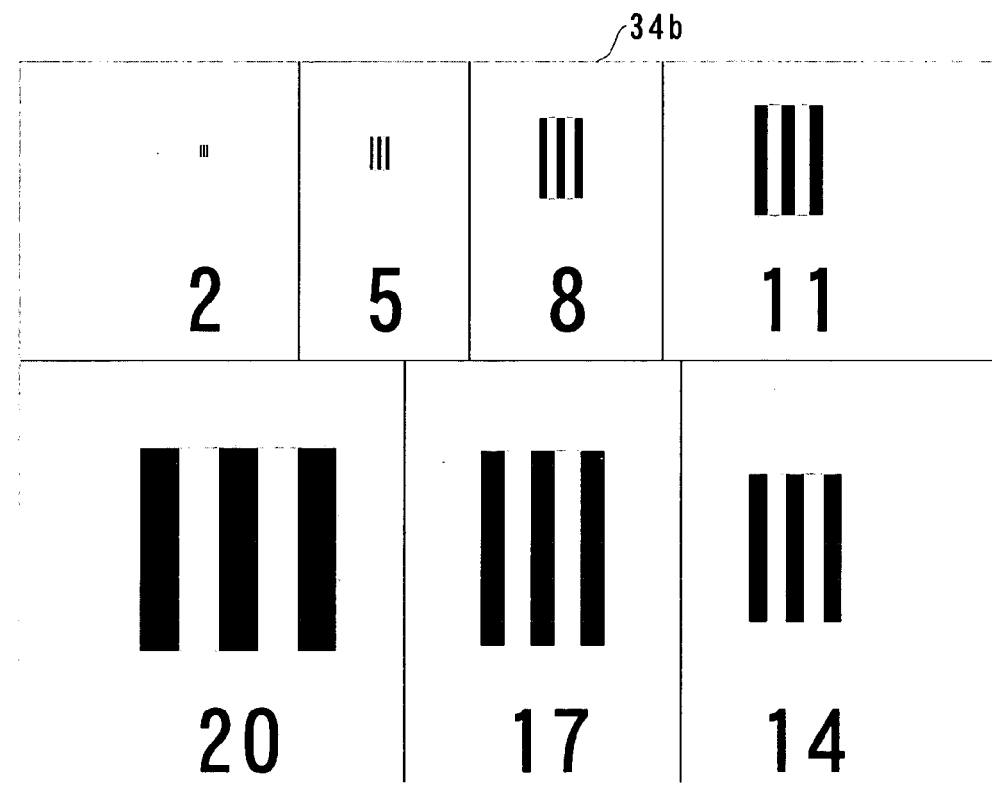
FIG. 14 is a schematic view showing another piece of vision test chart image data indicative of an arrangement of a plurality of targets.
Figure 15:
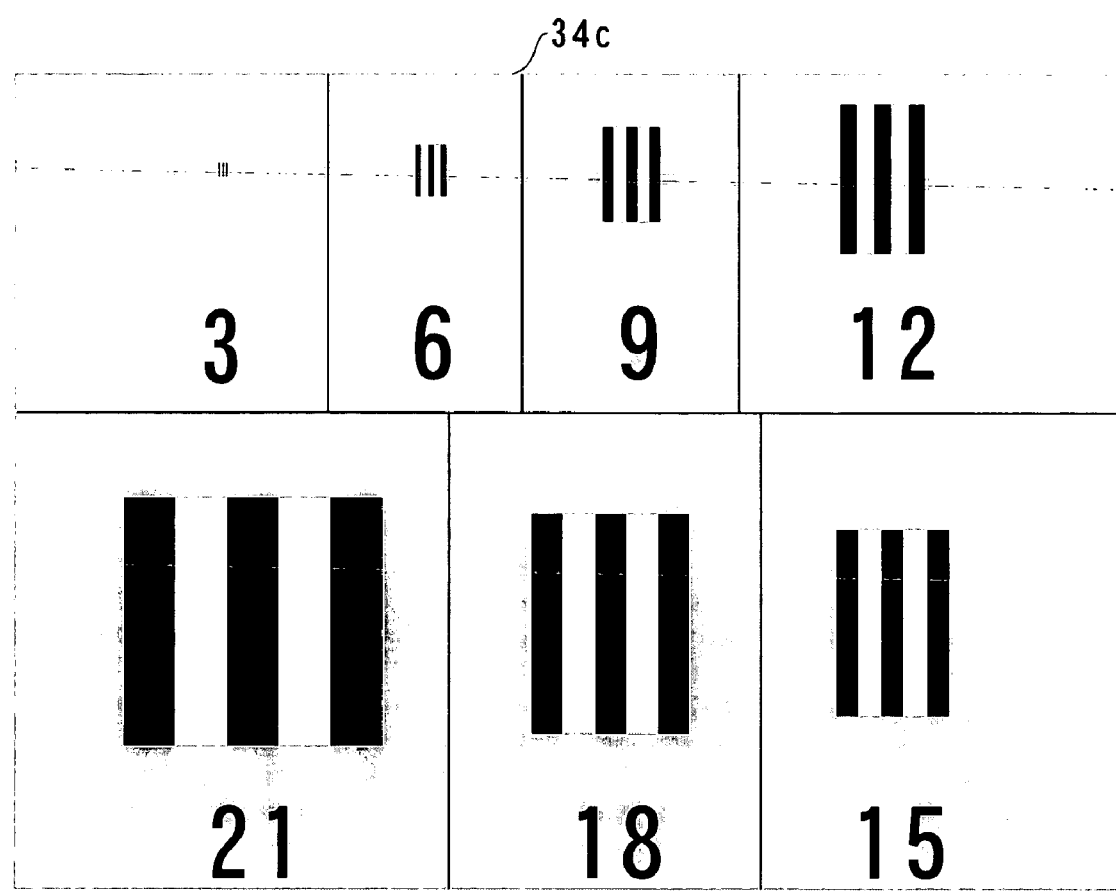
FIG. 15 is a schematic view showing still another piece of vision test chart image data indicative of an arrangement of a plurality of targets.

As the vision test chart image data 34 employed in the present invention, three pieces of vision test chart image data 34a, 34b, and 34c, shown in FIGS. 13 to 15, are used in combination to perform accurate visual acuity measurements. The vision test chart image data 34 is image data indicative of targets used to measure the far point vision, the targets having a light and dark line image made up of three black lines and two white lines of a certain line width. The target sizes (line widths) are different from each other in 21 levels corresponding to visual acuity. The targets are arranged on a green background. A white background may cause miosis which results in a greater depth of field in the eyes due to its excessive brightness, thus, causing a problem of providing an apparent visual acuity better than an actual visual acuity. This is why an eye-friendly green based color is used for the background to reduce brightness. Furthermore, in this preferred embodiment, since the subject is allowed to select the target in which the subject can distinguish its three lines, the subject can make a determination more easily as compared with the case of the Landoldt ring in which the subject is required to visually identify a single gap.

As shown in FIGS. 13 to 15, the vision test chart image data 34a, 34b, 34c is image data indicative of a vision measurement table that includes an arrangement of a plurality of different sized targets in one piece of image data. Targets of adjacent size levels are distributed among the pieces of vision test chart image data 34a, 34b, 34c such that the targets are included in more than one piece of vision test chart image data 34a, 34b, or 34c.

Now, this preferred embodiment will be explained in accordance with a specific example. The targets used in this preferred embodiment are arranged so as to increase in size as the numbers indicated below the targets increase from one to 21. In this case, targets numbered N and N+1, which are adjacent to each other in size level with a level difference of one, are not included in the same vision test chart image data. This is because any targets adjacent to each other in size level are only slightly different from each other in size, which may confuse the subject about which target to select.

For the vision test charts according to this preferred embodiment, three vision measurement tables, each table having a combination of targets having a size level difference of three, are employed to perform visual acuity measurements. The vision test chart image data 34a includes an arrangement of targets numbered 1, 4, 7, 10, 13, 16, and 19, the vision test chart image data 34b includes an arrangement of targets numbered 2, 5, 8, 11, 14, 17, and 20, and the vision test chart image data 34c includes an arrangement of targets numbered 3, 6, 9, 12, 15, 18, and 21. With these arrangements, the targets that are substantially different from each other in size level are included in the same image, allowing the subject to select a target therefrom that is clearly identified, thereby making it easy for the subject to indicate his/her preference.

The vision test chart image data 34 may provide images of different sizes in practice depending on the type of the display device of the subject computer 1 (a CRT or liquid crystal display), its size (such as 14 inches or 17 inches), and its screen resolution (such as horizontal pixels 800 times vertical pixels 600 or horizontal pixels 1026 times vertical pixels 768). Thus, a plurality of pieces of data indicative of images of different sizes and resolutions is stored to provide an image of the same size on any display devices.

The CGI 22 is connected with the optometric function portion 80 serving as the recognizable target determination unit. The optometric function portion 80 determines the subject's smallest recognizable target to thereby measure the subject's visual acuity, based on the preference data for the target that has been extracted and acquired by the CGI 22 and selected by the subject. The operation of the optometric function portion 80 will be detailed later in conjunction with the explanation of the operation of this preferred embodiment.

The subject computer 1 is a terminal for performing visual acuity measurements by communicating various pieces of data with the optometric server 10. As the subject computer 1, the subject can use a computer available at home, such as a personal computer or a workstation. Like the optometric server 10, the subject computer 1 which is provided with a modem and a network interface card (not shown) is adapted to communicate data with the optometric server 10 via the Internet 2. The display device of the subject computer 1 which displays images, such as the vision test chart image data, preferably has a display resolution that allows the vision test chart image data to be displayed on a single screen.

The subject computer 1 is provided with a WWW browser. The subject accesses the WWW server 20 by entering an IP address or URL, allocated to the optometric server 10, in the URL input field of the WWW browser. The WWW browser displays the vision test chart image data 34, transmitted from the WWW server 20, as required to perform a visual acuity measurement.

Figure 16:
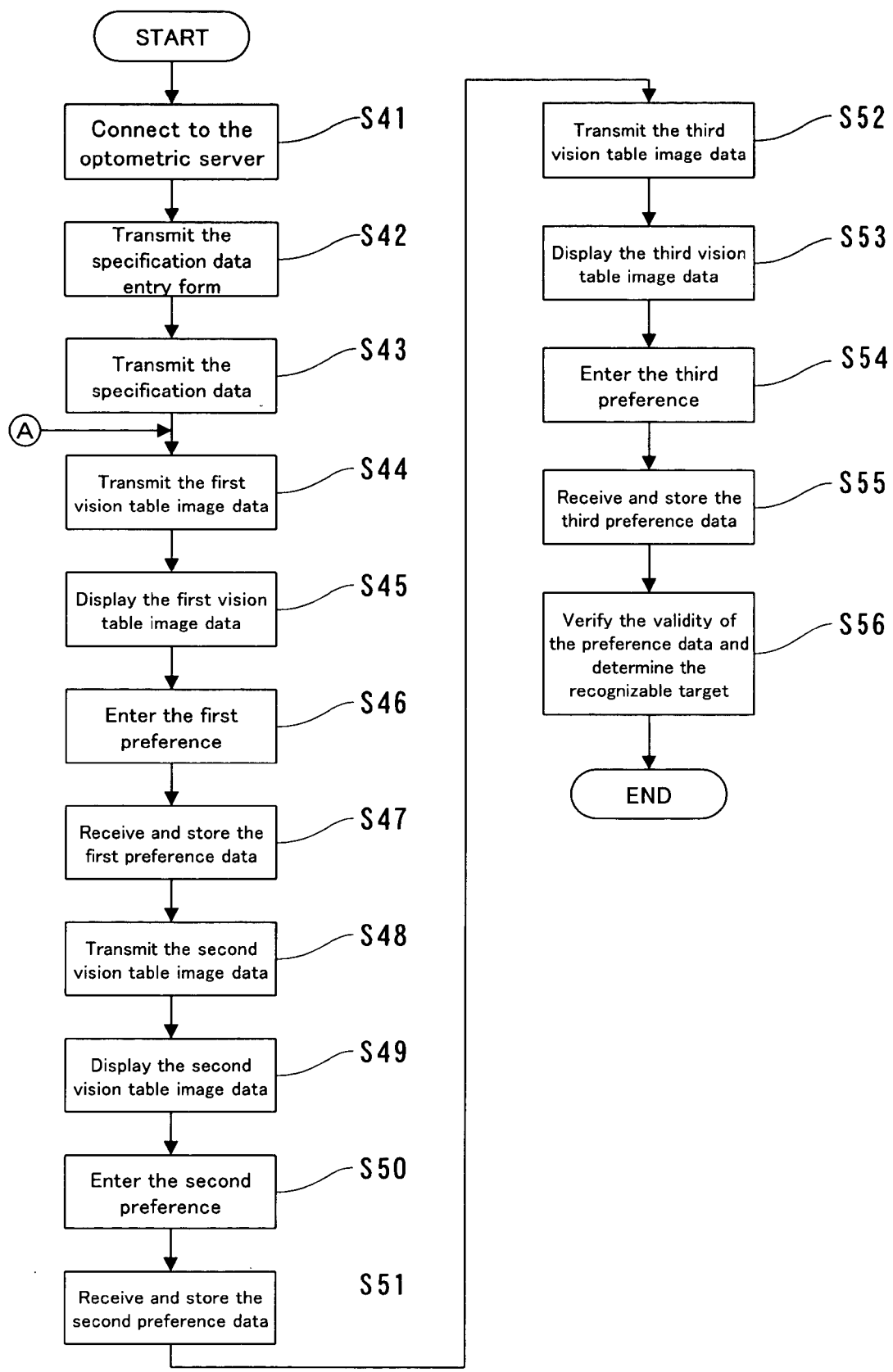
FIG. 16 is a flowchart showing an operation flow according to another preferred embodiment of the present invention.

Now, the operation of this preferred embodiment will be described with reference to FIG. 16.

First, the subject enters a URL in the WWW browser of the subject computer 1 to connect the subject computer 1 to the optometric server 10 (S41).

The optometric server 10 connected with the subject computer 1 transmits, to the subject computer 1, HTML data indicative of the form for entering the size and screen resolution of the display device of the subject computer 1 via the WWW server 20 (S42).

On the display device of the subject computer 1 which has received the HTML data indicative of the form for entering the specifications of the display device, the form is displayed to make an inquiry about the specifications of the display device. Using the mouse and keyboard, the subject enters the specifications of the display device of the subject computer 1 being used by the subject into the form as appropriate. After the entry, the subject clicks on the "Send" button provided in the form to thereby transmit the entered data to the optometric server 10 in the form of HTML data (S43).

The WWW server 20 receives the transmitted HTML data, which is then passed to the CGI 22. The CGI 22 extracts the data entered by the subject. Then, based on the contents of the data, the CGI 22 incorporates the vision test chart image data 34*a* or the first vision test chart image data corresponding to the display device of the subject computer 1 into the HTML data 24, which is then transmitted to the subject computer 1 (S44).

On the screen of the subject computer 1 which has received the vision test chart image data 34*a*, the vision test chart image data 34*a* is displayed as a vision test chart image (S45)

The subject views the vision test chart at a certain distance from the display device. Then, the subject uses the mouse and keyboard to enter the number given to the smallest of the targets that can be clearly recognized in the vision test chart displayed (S46).

The number or the first preference data entered by the subject is transmitted to the optometric server 10, and then supplied via the WWW server 20 and the CGI 22 to the optometric function portion 80 for storage (S47).

The optometric server 10 repeatedly executes the processing in steps S44 to S47 so that the same processing is also performed on the vision test chart image data 34*b* and 34*c* (S48 to S55).

Subsequently, the optometric server 10 that has received and stored the preferences for the first, second, and third vision test charts allows the optometric function portion 80 to evaluate the validity of the preferences. If valid, the optometric function portion 80 determines the subject's smallest recognizable target (S56).

Figure 17:
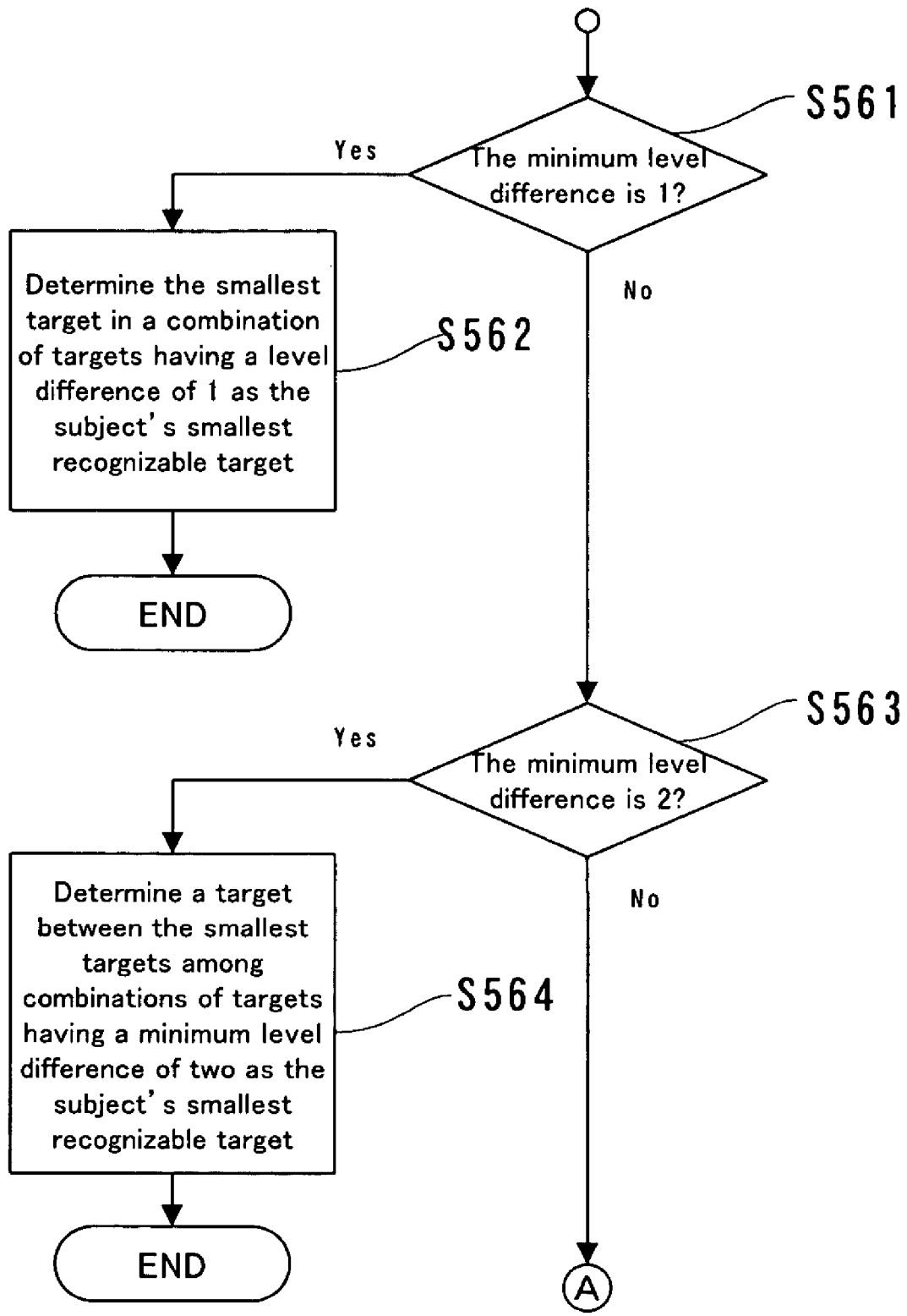
FIG. 17 is a flowchart showing a decision and operation flow followed by recognizable target determination unit.
Figure 20:
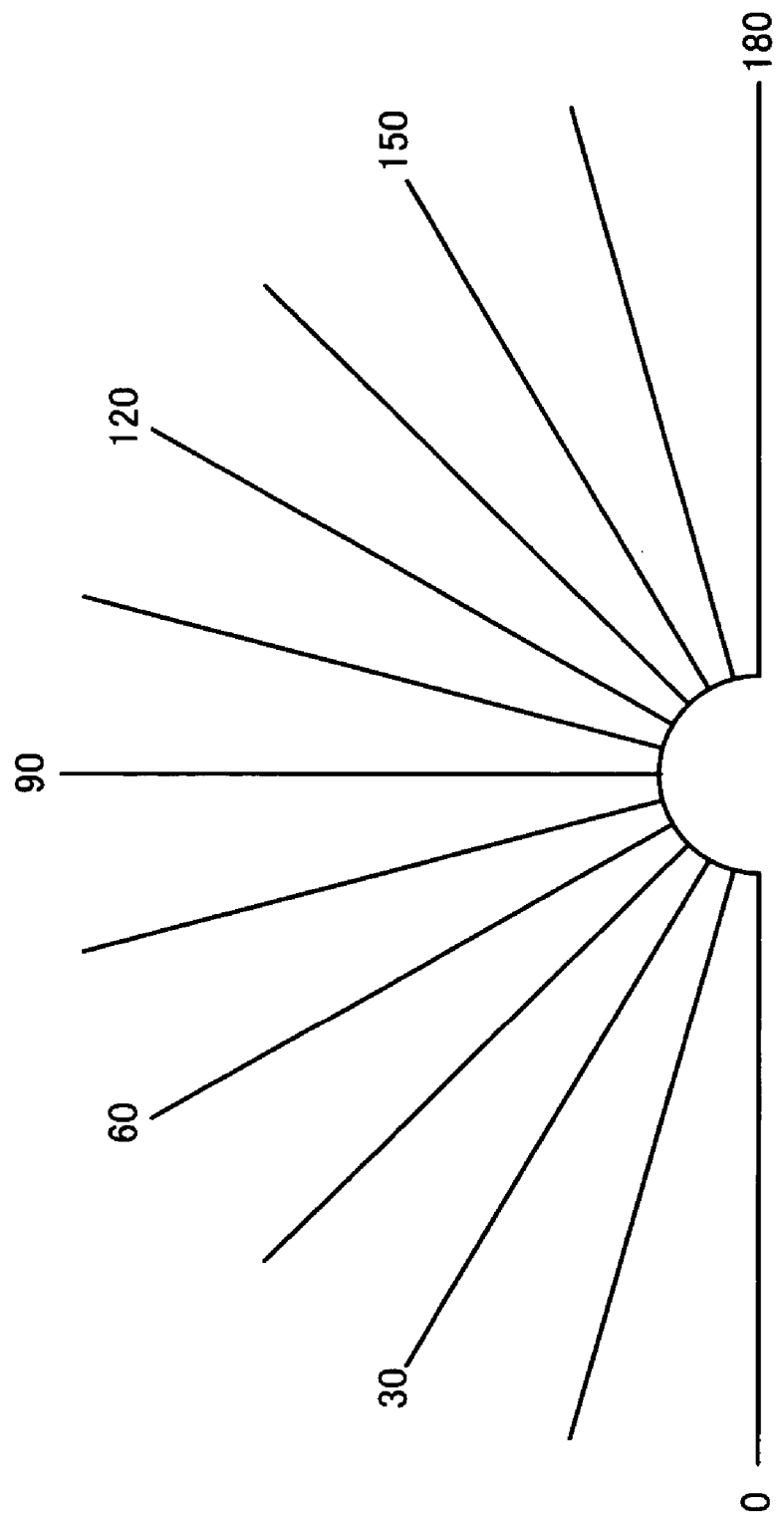
FIG. 20 is a view showing an example of an astigmatic dial.

Now, the flow in step S56 in which the optometric function portion 80 evaluates the validity of the preferences and determines the target will be explained in accordance with several examples of preferences for targets with reference to FIG. 17.

First, the optometric function portion 80 sorts the entered preferences for targets selected on the first, second, and third vision test charts in an order of size to determine whether there is a combination of adjacent targets having a minimum level difference of one (S561). For example, suppose that the subject has selected target No. 4 on the first vision test chart, target No. 5 on the second vision test chart, and target No. 6 on the third vision test chart. In this case, when the targets selected on the first, second, and third vision test charts are sorted in an order of size, the combination of the adjacent targets has a minimum level difference of one. In this case, the determination is made assuming that the subject has indicated the preferences without any error for the targets that the subject has clearly recognized on all the vision test charts. Then, the system employs target No. 4 as the smallest one that the subject can visually recognize to calculate his visual acuity (S562). When there is no combination of targets having a minimum level difference of one, the targets having been selected on the first, second, and third vision test charts and entered by the subject at the beginning, the system proceeds to step S563.

Then, the optometric function portion 80 sorts the entered preferences for targets in an order of size which have been selected on the first, second, and third vision test charts, and then determines whether there is a combination of adjacent targets having a minimum level difference of two (S563). For example, suppose that the subject has selected target No. 4 on the first vision test chart, target No. 8 on the second vision test chart, and target No. 6 on the third vision test chart. In this case, when the targets selected on the first, second, and third vision test charts are sorted in an order of size, the combination of the adjacent targets has a minimum level difference of two. With such preferences expressed, it can be said that a preference for any of the targets selected on the first, second, and third vision test charts has been entered with a mistake in decision. In this case, an average of the two smaller targets of those selected (No. 5 in this case) is determined as the smallest target that has been clearly recognized by the subject to calculate the subject's visual acuity.

In the aforementioned example, the average of the two smaller targets was employed to determine the smallest target that can be visually recognized by the subject. However, the present invention is not limited thereto. The present invention may also be configured to perform the selection of targets again.

On the other hand, the optometric function portion 80 makes no determination of the subject's smallest recognizable target when the entered preferences for targets selected on the first, second, and third vision test charts are sorted in an order of size, resulting in a combination of the adjacent targets having a minimum level difference of three or more. For example, suppose that the subject has selected target No. 4 on the first vision test chart, target No. 8 on the second vision test chart, and target No. 12 on the third vision test chart. In this case, when the targets selected on the first, second, and third vision test charts are sorted in an order of size, the combination of the adjacent targets has a minimum level difference of three, and thus, no combinations of the selected targets having a level difference of two or less are available. Since there is no consistency in such preferences for targets, it can be determined that the subject has indicated the preferences wrongly. In this case, the system makes no determination of the subject's smallest recognizable target, but returns to step S44 to repeat the selection procedure. On the other hand, this preferred embodiment is intended to repeat the selection procedure again. However, the system may not repeat the selection procedure but go to an error routine, thereby determining no visual acuity.

In this preferred embodiment, when the entered preferences for targets selected on the first, second, and third vision test charts are sorted in an order of size, and at least one combination of adjacent targets has a minimum level difference of two or less, the system determines the subject's smallest recognizable target. However, the present invention is not limited thereto. Alternatively, the system may also employ an allowable level difference of two or more or less depending on the accuracy of the visual acuity measurement to be performed. In this case, the smaller the allowable level difference, the better the accuracy of the visual acuity measurement becomes, whereas the greater the allowable level difference, the worse the accuracy of the visual acuity measurement becomes.

In this preferred embodiment, when the entered preferences for targets selected on the first, second, and third vision test charts are sorted in an order of size, and at least one combination of adjacent targets having a minimum level difference of two or less is available, the system determines the subject's smallest recognizable target. However, the present invention is not limited thereto. Alternatively, when a combination of adjacent targets having a predetermined level difference or more, e.g., two or more is available, the system may not determine the subject's smallest recognizable target, but repeat the selection of targets or go to an error routine to make no determination on the subject's visual acuity.

As described above, the optometric system according to this preferred embodiment enables the subject to readily determine the target whose features can be clearly recognized by the subject. Even when the subject has selected a wrong target, the system can determine objectively whether the selected target (chart) is a proper preference.

On the other hand, this preferred embodiment is adapted to use targets of three black lines and two white lines for visual acuity measurements. However, the present invention is not limited thereto. Alternatively, as illustrated in FIGS. 18(a) to 18(p), the system may use any targets conventionally employed for visual acuity measurements such as Landoldt rings, symbols, or characters, or any other targets as long as they are made up of graphics or characters which serve as targets.

This preferred embodiment is also adapted to measure the far point vision. However, the present invention is not limited thereto. Alternatively, the system may also use the vision test chart image data indicative of near point vision measurement targets to make near point vision measurements.

In this preferred embodiment, the visual acuity measurement is made without measuring the astigmatic axis of the subject. However, a subject with a considerable degree of astigmatism may suffer a problem of being incapable of accurately measuring his visual acuity. Thus, after the measurement of the astigmatism axis of the subject, it is preferable to display vision test charts (vision test chart image data) by taking the astigmatic axis of the subject into account, e.g., by aligning the orientation of the lines in the displayed dark and light image with the orientation of the astigmatic axis for measurement.

This preferred embodiment is also adapted to make visual acuity measurements using the three pieces of vision test chart image data 34a, 34b, 34c. However, the present invention is not limited thereto. Alternatively, the system may also employ two or more pieces of vision test chart image data for visual acuity measurements. The number of vision test charts (vision test chart image data) employed for visual acuity measurements is preferably increased or decreased depending on the number of targets employed.

This preferred embodiment is also adapted such that when a plurality of vision test charts are displayed again on the screen display unit to allow the subject to select the smallest recognizable target, the previously presented vision measurement table is employed as it is. However, the present invention is not limited thereto. Alternatively, with the level difference between targets increased or decreased, a plurality of vision test charts having a target level difference other than that of targets included in the plurality of previously presented vision test charts to allow the subject to select the smallest recognizable target. In this case, it is preferable to use a vision test chart having a level difference greater than that of the previously presented vision measurement table.

This preferred embodiment prepares and pre-stores a plurality of pieces of vision test chart image data. However, the present invention is not limited thereto. Alternatively, a plurality of pieces of target image data indicative of targets may be prepared, and combined to produce a vision test chart image as appropriate. Alternatively, one piece of target image data may be zoomed to produce a vision test chart image as appropriate.

This preferred embodiment makes measurements using vision test charts, each including three or more targets, so as to determine the subject's smallest recognizable target. However, the present invention is not limited thereto. For example, the system may display two smaller and larger targets having a level difference of two or more, either of which is selected by the subject, and then display targets smaller and larger than the selected one and different from the selected target by a level difference of two or more, allowing the subject to select the displayed targets. The system may repeat this step to determine the subject's smallest recognizable target.

This preferred embodiment also uses a WWW server to communicate data such as vision test chart image data or preference data. However, the present invention is not limited thereto. Alternatively, the optometric server application of the present invention may be installed in an optometric server for execution.

To display the vision measurement chart and the near point distance measurement chart in the aforementioned preferred embodiments, their images are displayed on a computer screen in the orientation selected upon determination of the astigmatic axis and an orientation perpendicular thereto. However, an image may be selected for display from among those in the four orientations pre-stored in the display screen database 30. Alternatively, data indicative of an image in a particular orientation may be pre-stored such that another image in another orientation may be produced by rotating the previous image using a graphics tool based on orientation data. Alternatively, drawing data indicative of an image to be displayed may be stored to draw and thereby produce the image using a drawing tool based on orientation data. As described above, a method for creating an image using the graphics tool may be employed with a load increase on image display. However, the method enables images to be created in any orientations, thereby readily expanding the orientations of astigmatic axes.

Likewise, to display a plurality of charts having various line widths for far point vision measurements, the graphics tool may also be used to zoom data indicative of an image having a particular line width or the drawing tool may be used to create images.

As described above, in the aforementioned preferred embodiment, the screen display sizes of the astigmatic axis determination chart, the vision measurement chart, and the near point measurement chart are not to be changed specifically by computer settings. However, the present invention is not limited thereto. Alternatively, to determine refractive powers with higher accuracy, computer screen settings may be acquired to change the screen display size based thereon. The computer screen settings to be acquired include the type and size of the display device and the resolution setting provided by the computer. These settings may be either acquired automatically as the computer property information or entered by the subject as his/her attribute data.

In this case, as in the foregoing, the graphics tool may be employed to zoom images or the drawing tool may be used to draw images.

As described above, in the aforementioned preferred embodiments, the astigmatic axis determination chart, the vision measurement chart, and the near point distance measurement chart are displayed in the optimum colors that have been empirically determined. However, the present invention is not limited thereto. Alternatively, it is also acceptable to provide a function for selecting display colors.

For example, the system may elicit a preference from the subject for sample colors that are presented to the subject in advance, or may allow the subject to select a color for display from among those that have been automatically pre-defined through screen settings provided by the computer.

The system may also pre-store a plurality of color patterns to display each chart, allowing the subject to select one from among them, or may employ the graphics tool to convert a particular display color pattern for an image to another display color pattern or employ the drawing tool to draw an image in a particular display color pattern.

Likewise, as described above, in the aforementioned preferred embodiments, the background and lines of the astigmatic axis determination chart, the vision measurement chart, and the near point distance measurement chart are displayed in the optimum brightness that has been empirically determined. However, the present invention is not limited thereto. Alternatively, it is also acceptable to provide a function of selecting display brightness.

The system may also pre-store a plurality of display brightness patterns to display each chart, allowing the subject to select one from among them, or may employ the graphics tool to convert a particular display brightness pattern for an image to another display brightness or employ the drawing tool to draw an image in a particular display brightness pattern.

As described above, in the aforementioned preferred embodiments, the system acquires the subject's attribute data each time an optometric service is provided to the subject. However, the present invention is not limited thereto. Alternatively, the system may pre-store the attribute data in a client database, from which a particular piece of data is extracted as required. As such, the system may be provided with the client database to store the aforementioned subject attribute data, as well as data on the history of the previously provided optometric services and on the eyeglasses and contact lenses that have been sold previously. This enables eye examinations to be provided with increased accuracy based on the features of the subjects and recommending further optimized lenses to the subjects.

As described above, in the aforementioned preferred embodiments, the system provides eye examinations mainly for near-sighted subjects with astigmatism. However, this preferred embodiment is adapted to acquire the near point distance in addition to the far point distance, thereby allowing for performing eye examinations on subjects with hyperopia or presbyopia based thereon.

That is, when the far point distance is very long with the near point distance being also long, the subject may possibly have hyperopia or presbyopia, which could be distinguished based on the accommodation power of the subject's eyes, if any.

In this context, for example, the refractive power of a subject with hyperopia or presbyopia may be calculated using a neural network which has been taught by a number of subjects with hyperopia or presbyopia. In this case, the neural network employs the age and sex of subjects as substitute parameters for the accommodation power of their eyes. The network also employs the far point distance, the near point distance, and the subject's attributes (age and sex) as inputs, with the refractive power of a subject with hyperopia or presbyopia being employed as an output.

Alternatively, the system may positively measure the accommodation power of the subject's eyes on a computer screen to determine the refractive power of the subject with hyperopia or presbyopia based thereon. To this end, for example, such methods may be conceivably employed for measuring the capability of tracking an image moving on the computer screen or for measuring the visual recognizability of the subject moving back and forth so as to quickly vary the distance between the subject and the computer screen.

These methods would provide an optometric system which can be utilized by any subjects, i.e., not only near-sighted subjects with astigmatism but also subjects with hyperopia or presbyopia.

As described above, in the aforementioned preferred embodiments, the system allows the optometric server connected to the Internet to provide optometric services. However, the present invention is not limited thereto. Alternatively, the system may also provide optometric services via a LAN or WAN within a particular organization.

Furthermore, the optometric apparatus according to the present invention may not only be employed to provide optometric services to subjects via a network but also may be installed at shops to provide optometric services on a standalone basis.

On the other hand, the method according to the present invention can also be implemented on a general personal computer. Accordingly, a personal computer executable program describing the method according to the present invention may be supplied to a subject to perform optometric services. The computer program may be supplied to the users in the form of a storage medium such as CD-ROMs or by allowing the user to download the program via the Internet.

As described above, the present invention provides the effects that a subject, including those with astigmatism, is allowed to readily make eye examinations on a computer screen without requiring a special piece of equipment. This is achieved by the steps of acquiring the attributes of the subject and an orientation selected by the subject on an astigmatic axis determination chart displayed on the computer screen, displaying vision measurement charts in the acquired orientation and the orientation perpendicular thereto to acquire visual recognition limits selected by the subject, calculating far point distances based on the acquired visual recognition limits and the acquired attributes of the subject, and calculating a refractive power based on the acquired orientation and the calculated two far point distances.

DESCRIPTION OF REFERENCE NUMERALS

1 Subject computer
2 Internet
10 Optometric server
20 WWW server
22 CGI
24 HTML data
30 Display screen database
32 Storage area
34 Vision test chart image data
34a, 34b, 34c Vision test chart image data
40 User interface means
50 Optometric information database
60 Far point calculation means
70 Power calculation means
80 Optometric function portion

The invention claimed is:

1. An optometric apparatus for performing an eye examination using a computer screen, comprising:
   a subject attribute acquisition unit for acquiring an attribute of a subject;
   an astigmatic axis determination chart display unit for displaying an astigmatic axis determination chart on the computer screen;
   an orientation acquisition unit for acquiring an orientation selected by the subject on the astigmatic axis determination chart displayed on the computer screen;
   a first vision measurement chart display unit for displaying on the computer screen a vision measurement chart having the acquired orientation;
   a first visual recognition limit acquisition unit for acquiring a visual recognition limit selected by the subject on the first vision measurement chart displayed on the computer screen;
   a second vision measurement chart display unit for displaying on the computer screen a vision measurement chart having an orientation perpendicular to the acquired orientation;
   a second visual recognition limit acquisition unit for acquiring a visual recognition limit selected by the subject on the second vision measurement chart displayed on the computer screen;
   a far point distance calculation unit for employing the acquired first visual recognition limit, the acquired second visual recognition limit, and the acquired subject attribute as entry parameters to calculate a first far point distance and a second far point distance; and
   a power calculation unit for calculating a refractive power based on the acquired orientation and the calculated first and second far point distances.

2. The optometric apparatus according to claim 1, wherein the first vision measurement chart display unit and the second vision measurement chart display unit include a display unit for sequentially displaying on the computer screen a plurality of vision test charts of a combination of targets having a size level difference of two or more; and
   the first visual recognition limit acquisition unit and the second visual recognition limit acquisition unit include a selection unit for allowing the subject to select the smallest recognizable target on each vision test chart displayed on the computer screen, and a determination unit for determining the subject's smallest recognizable target from the smallest recognizable targets selected on each vision test chart.

3. The optometric apparatus according to claim 2, wherein the display unit for sequentially displaying on the computer screen a plurality of vision test charts displays three vision test charts, each of the vision test charts including targets having a level difference of three.

4. The optometric apparatus according to claim 2, wherein the determination unit for determining the subject's smallest recognizable target from the smallest recognizable targets selected on each vision test chart includes a determination unit for determining the smallest target in a combination of targets having a size level difference of one as the subject's smallest recognizable target when the selection unit for selecting the smallest recognizable target on each vision test chart displayed on the computer screen has selected targets having a minimum level difference of one.

5. The optometric apparatus according to claim 2, wherein the determination unit for determining the subject's smallest recognizable target from the smallest recognizable targets selected on each vision test chart includes a determination unit for determining a target between the smallest targets in combination among combinations of targets having a minimum level difference of two as the subject's smallest recognizable target when the selection unit for selecting the smallest recognizable target on each vision test chart displayed on the computer screen has selected targets having a minimum level difference of two.

6. The optometric apparatus according to claim 2, wherein the determination unit for determining the subject's smallest recognizable target from the smallest recognizable targets selected on each vision test chart includes a selection unit for displaying a plurality of vision test charts again on the computer screen to allow the subject to select the smallest recognizable target on each of the plurality of vision test charts when the selection unit for selecting the smallest recognizable target on each vision test chart displayed on the computer screen has selected targets having a minimum level difference of three or more.

7. The optometric apparatus according to claim 1, wherein the far point distance calculation unit has a function of calculating a far point distance using a learn model which has been determined from a number of subjects based on a relationship between the subject's attribute and the visual recognition limit, and the far point distance.

8. The optometric apparatus according to claim 1, further comprising:
   a near point distance measurement chart display unit for displaying a near point distance measurement chart on the computer screen, and a near point distance acquisition unit for acquiring a near point distance entered by the subject on the near point distance measurement chart displayed on the computer screen.

9. The optometric apparatus according to claim 1, wherein the astigmatic axis determination chart display unit has a function of displaying four groups of a plurality of parallel lines, the four groups having lines arranged in different orientations.

10. The optometric apparatus according to claim 1, wherein at least one of the first vision measurement chart display unit and the second vision measurement chart display unit has a function of displaying a plurality of light and dark line images having different line widths.

11. The optometric apparatus according to claim 1, wherein at least one of the astigmatic axis determination chart display unit, the first vision measurement chart display unit, and the second vision determination chart display unit includes a screen display information acquisition unit for acquiring screen display information on the computer screen, and a display size rescale unit for rescaling the display size of the computer screen depending on the acquired screen display information.

12. The optometric apparatus according to claim 1, wherein at least one of the astigmatic axis determination chart display unit, the first vision measurement chart display unit, and the second vision determination chart display unit includes a display color selection unit for selecting a color to be displayed on the computer screen.

13. The optometric apparatus according to claim 1, wherein at least one of the astigmatic axis determination chart display unit, the first vision measurement chart display unit, and the second vision determination chart display unit includes a display brightness selection unit for selecting a brightness used for display on the computer screen.

14. An optometric method for performing an eye examination using a computer screen, the method comprising:
   a subject attribute acquisition step for acquiring an attribute of a subject;

an astigmatic axis determination chart display step for displaying an astigmatic axis determination chart on the screen;

an orientation acquisition step for acquiring an orientation selected by the subject on the astigmatic axis determination chart displayed on the computer screen;

a first vision measurement chart display step for displaying on the screen a vision measurement chart having the acquired orientation;

a first visual recognition limit acquisition step for acquiring a visual recognition limit selected by the subject on the first vision measurement chart displayed on the computer screen;

a second vision measurement chart display step for displaying on the screen a vision measurement chart having an orientation perpendicular to the acquired orientation;

a second visual recognition limit acquisition step for acquiring a visual recognition limit selected by the subject on the second vision measurement chart displayed on the computer screen;

a far point distance calculation step for employing the acquired first visual recognition limit, the acquired second visual recognition limit, and the acquired subject attribute as entry parameters to calculate a first far point distance and a second far point distance; and a power calculation step for calculating a refractive power based on the acquired orientation and the calculated first and second far point distances.

15. The optometric method according to claim 14, wherein the first and the second vision measurement chart display steps include a display step for sequentially displaying on the computer screen a plurality of vision test charts of a combination of targets having a size level difference of two or more; and the first visual recognition limit acquisition step and the second visual recognition limit acquisition step include a selection step for allowing the subject to select the smallest recognizable target on each vision test chart displayed on the computer screen, and a determination step for determining the subject's smallest recognizable target from the smallest recognizable targets selected on each vision test chart.

16. An optometric server for providing a function of performing an eye examination using a computer screen to a client computer connected to a network, the server comprising:

a subject attribute acquisition unit for acquiring an attribute of a subject;

an astigmatic axis determination chart display unit for displaying an astigmatic axis determination chart on the computer screen;

an orientation acquisition unit for acquiring an orientation selected by the subject on the astigmatic axis determination chart displayed on the computer screen;

a first vision measurement chart display unit for displaying on the computer screen a vision measurement chart having the acquired orientation;

a first visual recognition limit acquisition unit for acquiring a visual recognition limit selected by the subject on the first vision measurement chart displayed on the computer screen;

a second vision measurement chart display unit for displaying on the computer screen a vision measurement chart having an orientation perpendicular to the acquired orientation;

a second visual recognition limit acquisition unit for acquiring a visual recognition limit selected by the subject on the second vision measurement chart displayed on the computer screen;

a far point distance calculation unit for employing the acquired first visual recognition limit, the acquired second visual recognition limit, and the acquired subject attribute as entry parameters to calculate a first far point distance and a second far point distance; and a power calculation unit for calculating a refractive power based on the acquired orientation and the calculated first and second far point distances.

17. An optometric server for performing eye examinations, which provides a vision test chart to a client terminal connected to a network, the vision test chart including a plurality of targets having sizes varied in a stepwise manner corresponding to visual acuity, and allows a subject to select the smallest recognizable target on the vision test chart displayed on a computer screen of the client terminal, thereby allowing the subject to subjectively measure his visual acuity, the server comprising:

a vision test chart image data provision unit for providing vision test chart image data so that a plurality of vision test charts of a combination of targets having a size level difference of two or more are displayed sequentially on the computer screen of the client terminal;

a distinctive recognizable target acquisition unit for acquiring the smallest recognizable target selected by the subject on each vision test chart displayed on the computer screen of the client terminal; and a recognizable target determination unit for determining the subject's smallest recognizable target from each distinctive recognizable target acquired by the distinctive recognizable target acquisition unit.

18. An optometric method for performing an eye examination, in which a vision test chart including a plurality of targets having sizes varied in a stepwise manner corresponding to visual acuity is displayed on a computer screen and a subject is allowed to select the smallest recognizable target on the vision test chart displayed on the computer screen, thereby allowing the subject to subjectively measure his/her visual acuity, the method comprising the steps of:

sequentially displaying on the computer screen a plurality of vision test charts of a combination of targets having a size level difference of two or more;

allowing the subject to select the smallest recognizable target on each vision test chart displayed on the computer screen; and determining the subject's smallest recognizable target from the smallest recognizable targets selected on each vision test chart.

* * * * *